(12) United States Patent
Keppler et al.

(10) Patent No.: US 11,627,979 B2
(45) Date of Patent: Apr. 18, 2023

(54) SURGICAL PLAN OPTIONS FOR ROBOTIC MACHINING

(71) Applicant: Stryker Corporation, Kalamazoo, MI (US)

(72) Inventors: Lou Keppler, Lakewood, OH (US); Sathiya Prabaharan, Parsippany, NJ (US); Emily Hampp, Far Hills, NJ (US); Stuart L. Axelson, Jr., Succasunna, NJ (US); John R. Fossez, Frisco, TX (US)

(73) Assignee: Stryker Corporation, Kalamazoo, MI (US)

( * ) Notice: Subject to any disclaimer, the term of this patent is extended or adjusted under 35 U.S.C. 154(b) by 238 days.

(21) Appl. No.: 16/877,714

(22) Filed: May 19, 2020

(65) Prior Publication Data

US 2020/0275943 A1    Sep. 3, 2020

Related U.S. Application Data

(63) Continuation of application No. 14/461,002, filed on Aug. 15, 2014, now abandoned.

(51) Int. Cl.
| A61B 17/15 | (2006.01) |
| A61B 34/30 | (2016.01) |
| A61B 17/17 | (2006.01) |
| A61B 17/32 | (2006.01) |
| A61B 90/11 | (2016.01) |

(52) U.S. Cl.
CPC ............ *A61B 17/32* (2013.01); *A61B 17/155* (2013.01); *A61B 17/157* (2013.01); *A61B 34/30* (2016.02); *A61B 17/1764* (2013.01); *A61B 90/11* (2016.02)

(58) Field of Classification Search
CPC . A61B 17/155; A61B 17/157; A61B 17/1764; A61B 17/32; A61B 34/30; A61B 90/11
See application file for complete search history.

(56) References Cited

U.S. PATENT DOCUMENTS

| 6,676,669 B2 | 1/2004 | Charles et al. |
| 6,702,805 B1 | 3/2004 | Stuart |
| 6,723,106 B1 | 4/2004 | Charles et al. |
| 7,892,243 B2 | 2/2011 | Stuart |
| 7,950,306 B2 | 5/2011 | Stuart |
| 2003/0005786 A1 | 1/2003 | Stuart et al. |

(Continued)

OTHER PUBLICATIONS

Stryker Navigation, Precision Knee Navigation Operative Technique, pp. 1-40 (2007).

*Primary Examiner* — Samuel S Hanna
(74) *Attorney, Agent, or Firm* — Lerner David LLP

(57) ABSTRACT

A method of performing surgery on a bone includes providing a robotically controlled bone preparation system and creating at least one hole in the bone with the robotically controlled bone preparation system prior to machining the bone. The bone hole aligns with a hole or a post in a guide for a manual cutting tool. If the robot fails during surgery, or if the surgeon does not wish to complete the procedure with the robot, the guide is attached to the bone after aligning the guide hole with the bone hole. The surgery is completed manually after the guide is attached to the bone, and the robot is not used after the guide is attached to the bone.

16 Claims, 22 Drawing Sheets

(56) References Cited

U.S. PATENT DOCUMENTS

| | | | |
|---|---|---|---|
| 2006/0142657 A1* | 6/2006 | Quaid | A61B 90/37 |
| | | | 600/424 |
| 2007/0173946 A1* | 7/2007 | Bonutti | A61B 17/1717 |
| | | | 623/20.14 |
| 2010/0268249 A1 | 10/2010 | Stuart | |
| 2010/0268250 A1 | 10/2010 | Stuart et al. | |
| 2010/0275718 A1 | 11/2010 | Stuart et al. | |
| 2011/0029093 A1* | 2/2011 | Bojarski | A61F 2/30942 |
| | | | 623/20.14 |

\* cited by examiner

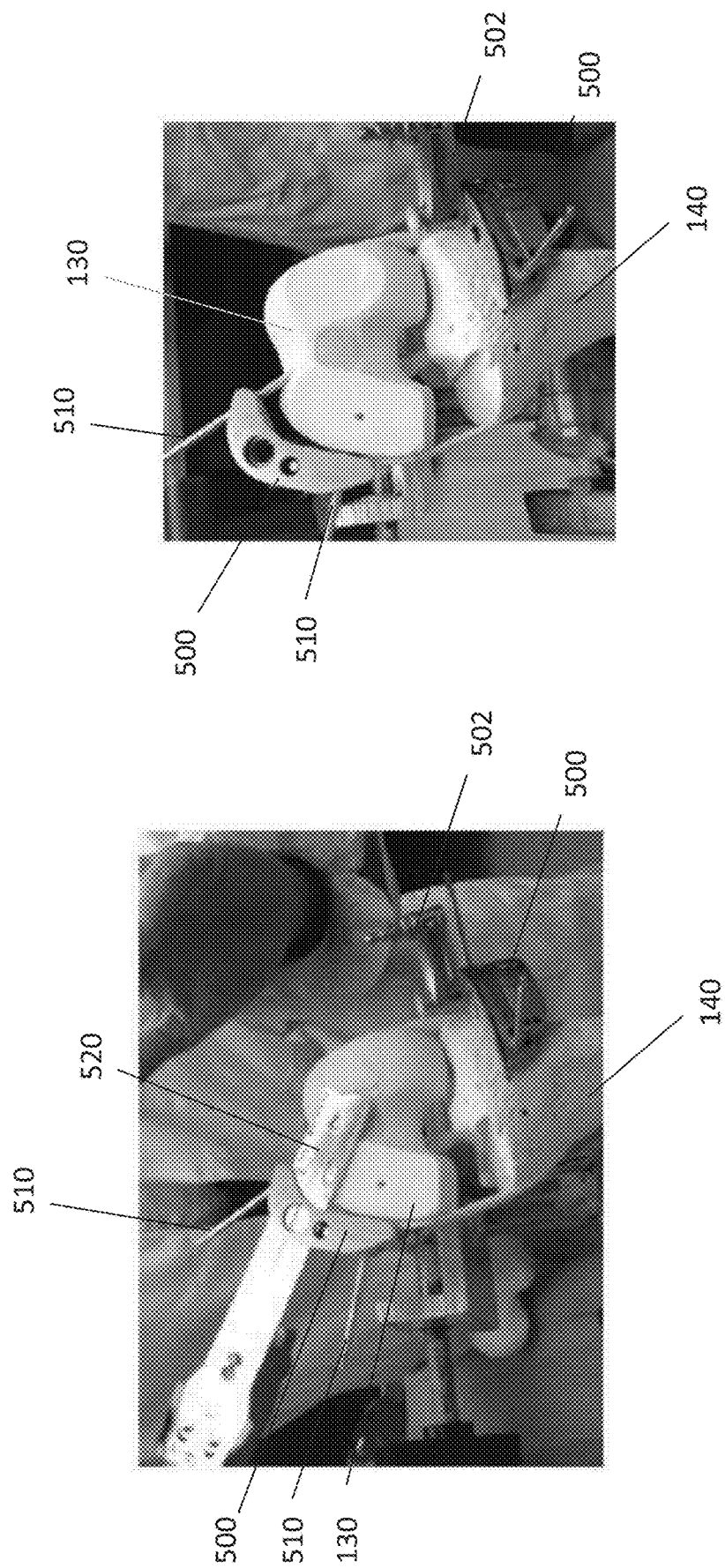

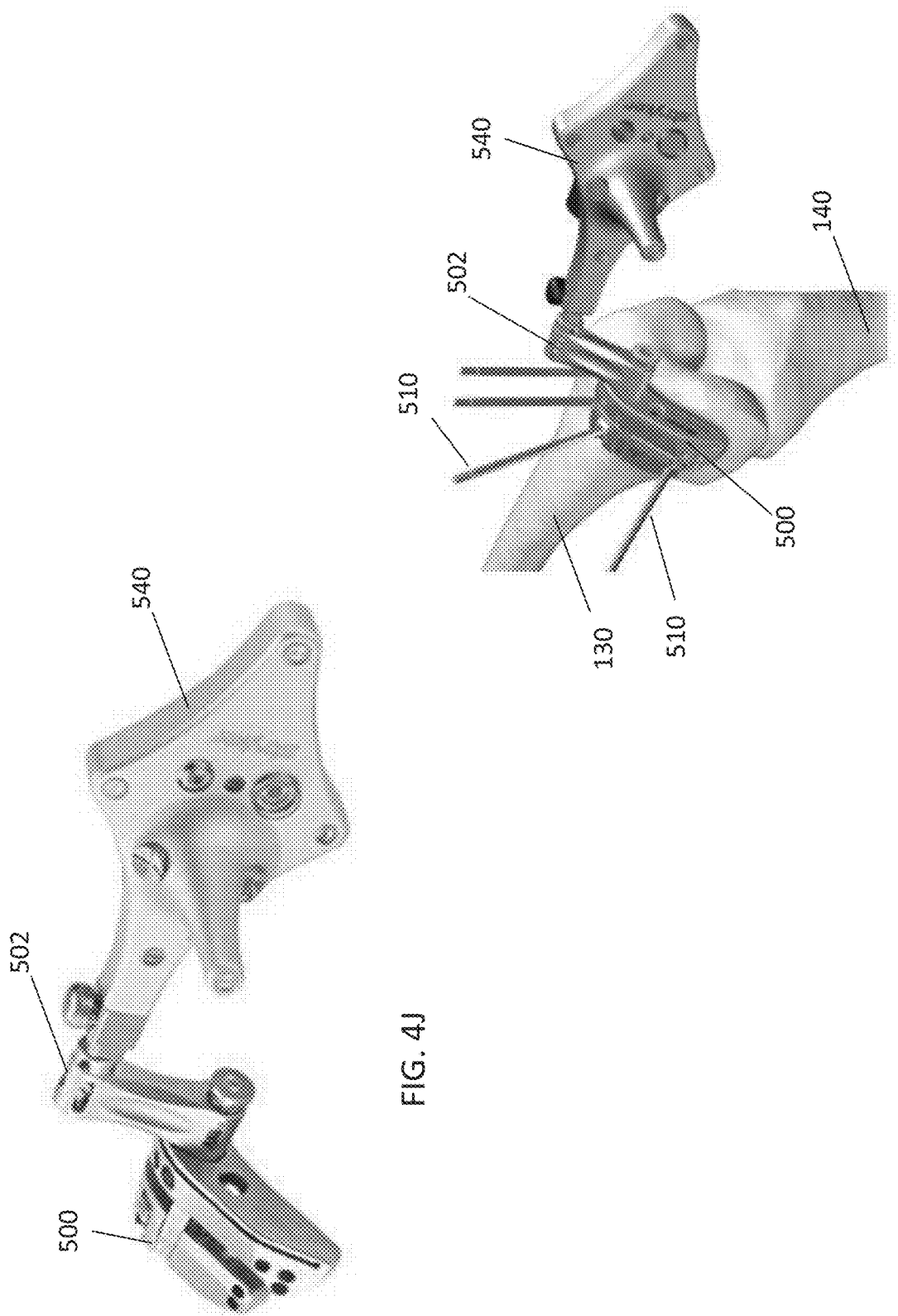

SURGICAL PLAN OPTIONS FOR ROBOTIC MACHINING

CROSS-REFERENCE TO RELATED APPLICATIONS

This application is a continuation of U.S. patent application Ser. No. 14/461,002, filed Aug. 15, 2014, the disclosure of which is hereby incorporated by reference herein.

FIELD OF THE INVENTION

The present invention relates to surgical options for navigated and/or robotic bone machining and in particular relates to having the option of completing joint arthroplasty procedures with conventional instruments following the use of navigated and/or robot based applications.

BACKGROUND OF THE INVENTION

In a traditional joint arthroplasty procedure, such as a total knee arthroplasty ("TKA") surgery, diseased bone and/or cartilage of a patient is generally removed and replaced with a prosthetic implant. A surgeon may resect the bone using a hand-held oscillating saw blade which results in a series of planar bone surfaces. Additionally, the surgeon may use a drill, broach or tamp instrument to make cylindrical holes into the bone in order to accommodate fixation features on the implant. The planar bone surfaces and cylindrical bone holes, for example, are generally oriented to interface with flat surfaces and pegs or keels of a prosthetic implant.

In such arthroplasty surgeries, the cartilage and/or bone of a patient may be prepared by a surgeon using conventional manual instrumentation. The instrumentation used may include, for example, planar resection guides, oscillating saws, drills, chisels, punches and reamers.

Robotic surgery may also be used in arthroplasty procedures, as well as in many different medical applications. The use of robotically controlled bone preparation systems allows for preoperatively planned bone preparation to be carried out with increased accuracy and repeatability. Further, when a milling or burring cutting tool is used, there may be opportunity to evolve to non-planar and non-cylindrical bone resections. Therefore, robotic preparation may be used with prosthetic implants having bone contacting geometries designed to optimize contacting surfaces and/or clearances with bone. Such implants generally have an increased ability to improve the load transfer through the implant-bone interface while considering patient kinematics and articular surface geometries.

Cartilage and/or bone may be prepared with the assistance of a robot in arthroplasty procedures. Robot assisted arthroplasty may include the use of the following, for example: implant specific software, milling/burring or other rotational cutting instruments and various levels of surgeon interface. For example, in one robot mode, the robot may perform the cartilage/bone preparation with the surgeon observing. In another robot mode, the surgeon may actually guide a cutting tool, such as a rotational cutting tool or saw, such as an oscillating or reciprocating saw, within a predetermined boundary or within a constrained boundary where manual milling is contained. In all modes, the surgeon must be able to stop the robotic preparation if required. Robotic technology may include that described in U.S. Pat. Nos. 6,676,669, 7,892,243, 6,702,805, 6,723,106, and 7,950,306 as well as U.S. Patent Application Nos. 2010/0268249, 2010/0268250, 2010/0275718, and 2003/0005786, the disclosures of all of which are hereby incorporated by reference in their entireties. Using robotic preparation may enable the development of new implant designs having substantially non-planar bone contacting geometries and improved fixation features, but potential drawbacks may exist. For example, current robotic surgical techniques may leave the surgeon without a contingency plan if the robotic device fails mid-surgery. In such a case, the surgeon may need to resort to using standard instruments to complete the particular procedure. However, the transition to standard instrumentation mid-procedure may be difficult, particularly if bony landmarks have already been resected. It would thus be desirable to have apparatus and methods to facilitate a surgeon transitioning from a robotic to manual procedure during a surgical procedure.

BRIEF SUMMARY OF THE INVENTION

In one exemplary surgical procedure, a robot-specific plan is created for a particular patient. This plan may involve, for example, precise non-planar cuts that would be difficult or even impossible for a surgeon to make manually. While such a robotic plan may provide for potential advantages over traditional manual plans using conventional tools and planar cuts, there is always a possibility that the robot may fail at any point during surgery. For example, the guidance system (also known as a navigation or "NAV" system) may stop working, or the robot itself may stop working properly.

If the robot fails mid-surgery, for example, the surgeon may need to use conventional instrumentation to complete the particular procedure. However, this may be difficult as bone has already been removed by the robot, generally with non-planar cuts. While conventional instrumentation is generally used in conjunction with planar cuts and with pre-drilled reference points, making the use of conventional instruments to finish the surgery with non-planar cuts at this point would be difficult. Even if the surgeon is able to complete the procedure after the robot has failed, the results are likely to be different than the preoperatively planned or originally intended results with the robot performing the procedure. With the foregoing in mind, the present invention includes contingency plans available for use in robotic surgical procedures to facilitate the surgeon quickly and easily completing the surgery according to the original plan if the robot fails mid-surgery. It should also be noted, as described in detail below, that the contingency plans may also be used when the surgeon intends to complete the procedure manually after a robot has performed some initial machining.

In one embodiment of the present invention, a method of performing surgery on a bone includes providing a robotically controlled bone preparation system to prepare the bone according to a preoperative surgical plan such that an implant can be coupled to the prepared bone in a preoperatively planned position and orientation. The preoperative surgical plan includes determining the location and orientation of one or more guide holes in the bone in order to complete the procedure with conventional instrumentation. According to this method, once the preoperative plan is created, navigated and/or robot machining is used to create the one or more guide holes in the bone. One or more conventional instruments such as an alignment rod, for example, is then located and oriented with respect to the bone using the one or more guide holes. In this embodiment, the conventional instruments are not being used based on a contingency plan, but are rather being used according to the preoperative plan.

In one embodiment of the present invention, a method of performing surgery on a bone includes providing a robotically controlled bone preparation system and creating at least one hole in the bone with the robotically controlled bone preparation system prior to machining the bone, wherein the at least one bone hole in the bone aligns with at least one hole or post in a guide for a manual cutting tool. The method may further include the step of initiating a debulking phase of the surgery with the robotically controlled bone preparation system after the step of creating at least one hole in the bone. The method may still further include the step of attaching the guide to the bone after aligning the at least one guide hole or post with the at least one bone hole. Still further, the method may include the step of completing the surgery manually after the step of attaching the guide to the bone, wherein the robotically controlled bone preparation system is not used after the guide is attached to the bone. The guide may include a tracker for use with a surgical navigation system.

In one embodiment, the completed surgery may be a total knee arthroplasty. The step of creating at least one hole in the bone may include creating at least two holes in a femur and at least two holes in a tibia. The step of attaching the guide to the bone may include attaching a femoral resection guide to the femur and/or attaching a tibial resection guide to the tibia.

In another embodiment, the completed surgical procedure may be a partial knee arthroplasty. The step of creating at least one hole in the bone may include creating at least two holes in a femur and at least two holes in a tibia. The step of attaching the guide to the bone may include attaching a femoral resection guide to the femur and/or attaching a tibial resection guide to the tibia. The step of completing the surgery manually may include manually debulking the femur facilitated by a surgical navigation system and/or manually debulking the tibia facilitated by a surgical navigation system.

In a further embodiment, the method includes the step of manually completing the surgery without further use of the robotically controlled bone preparation system after the robotically controlled bone preparation system creates the at least one bone hole.

In yet another embodiment of the invention, a method of performing surgery on a bone includes providing a robotically controlled bone preparation system to prepare the bone according to a preoperative surgical plan such that an implant can be coupled to the prepared bone in a preoperatively planned position and orientation. The method may also include creating at least one contingency hole in the bone with the robotically controlled bone preparation system prior to preparing the bone according to the preoperative surgical plan, wherein the position of the at least one contingency hole in the bone corresponds to at least one hole or post in a guide for guiding a manual cutting tool that could be used to prepare the bone according to the preoperative surgical plan. The method may further include removing at least one anatomical landmark of the bone after the step of creating at least one contingency hole in the bone, wherein the at least one anatomical landmark would have been used in determining a position and orientation of the guide with respect to the bone. The method may also include attaching the guide to the bone after aligning the at least one guide hole or post with the at least one contingency hole. The guide may include a tracker for use with a surgical navigation system. The surgery may be completed manually after the step of attaching the guide to the bone, wherein the robotically controlled bone preparation system is not used after the guide is attached to the bone. The method may also include manually debulking the femur and tibia facilitated by a surgical navigation system. The step of creating at least one contingency hole in the bone may include creating at least one contingency hole in a femur and at least one contingency hole in a tibia.

In still another embodiment of the invention a method of performing surgery on a bone includes providing a robotically controlled bone preparation system to prepare the bone according to a preoperative surgical plan. The method may also include operating the robotically controlled bone preparation system to machine the bone to have features corresponding to features of a manual cutting guide, and coupling the manual cutting guide to the bone. The method may also include operating the robotically controlled bone preparation system to further machine the bone such that at least one anatomical landmark is modified prior to coupling the manual cutting guide to the bone. The step of coupling the manual cutting guide to the bone may occur after the robotically controlled bone preparation system has at least partially failed to machine the bone according to the preoperative surgical plan. The step of operating the robotically controlled bone preparation system to machine the bone may include creating at least one hole in the bone. The at least one hole in the bone may correspond to at least one hole or post in the manual cutting guide. The method may also include attaching the manual cutting guide to the bone after aligning the at least one guide hole or post with the at least one hole in the bone. The guide may include a tracker for use with a surgical navigation system. The method may also include the step of completing the surgery manually after the step of attaching the guide to the bone, wherein the robotically controlled bone preparation system is not used after the guide is attached to the bone. The step of completing the surgery manually may include manually debulking the femur and tibia facilitated by a surgical navigation system.

In still a further embodiment of the invention, a method of performing surgery on a bone includes providing a robotically controlled bone preparation system to make bone resections, operating the robotically controlled bone preparation system to machine the bone to have features corresponding to features of a guide for guiding a manual cutting tool, coupling the guide to the bone, and resecting the bone with the manual cutting tool guided by the guide. The step of operating the robotically controlled bone preparation system to machine the bone may include creating at least one hole in the bone. The at least one hole in the bone may correspond to at least one hole or post in the guide. The method may also include attaching the guide to the bone after aligning the at least one guide hole or post with the at least one hole in the bone. The surgery may be completed manually after the step of attaching the guide to the bone, wherein the robotically controlled bone preparation system is not used in the surgery after the guide is attached to the bone. The guide may include a tracker for use with a surgical navigation system. The completed surgery may be a total knee arthroplasty. The step of creating at least one hole in the bone may include creating at least two holes in a femur and at least two holes in a tibia. The step of attaching the guide to the bone may include attaching a femoral resection guide to the femur and/or a tibial resection guide to the tibia. The completed surgery may also be a partial knee arthroplasty. The step of creating at least one hole in the bone may include creating at least two holes in a femur and at least two holes in a tibia. The step of completing the surgery manually may include manually resecting the femur and/or manually resecting the tibia facilitated by a surgical navigation system.

In yet another embodiment of the invention, a method of performing surgery on a bone includes providing a robotically controlled bone preparation system to make bone resections. The method may also include operating the robotically controlled bone preparation system to machine the bone to have features corresponding to features of a surgical instrument, wherein the robotic machining has at least one of increased accuracy, reproducibility, and speed compared to manual resections. The method may further include manually completing the surgery on the bone without further use of the robotically controlled bone preparation system, including the step of manually coupling the surgical instrument to the bone.

BRIEF DESCRIPTION OF THE DRAWINGS

FIG. 4G is a perspective view of a distal femoral cut being manually performed using bailout holes.

FIG. 4H is a perspective view of the distal femur after completion of the manual cut illustrated in FIG. 4F.

FIG. 4J is a perspective view of a one embodiment of a navigated MIS resection guide with a tracker attached by a tracker adapter.

FIG. 4K is a perspective view of the navigated MIS resection guide of FIG. 4I attached to a femur.

DETAILED DESCRIPTION

As used herein, the term "distal" means more distant from the heart and the term "proximal" means closer to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body. Terms including "debulking," "resecting," "machining," "finishing," and "bone preparation," are used interchangeably herein, and all generally refer to the removal and/or reshaping of bone.

In the figures, with particular reference to the flow charts contained therein, a step enclosed in a hexagon indicates a tool-change step, a step enclosed in a trapezoid indicates a knee-positioning step, a step in a parallelogram indicates a registration step, a step enclosed in a diamond may indicate a step which branches into multiple other possible steps, and a step enclosed in a rectangle indicates a bone preparation or trialing/implantation step, unless otherwise indicated. Further, a step or group of steps enclosed in a broken rectangle indicates that the steps contained therein may be alternative or optional steps.

Figure 1:
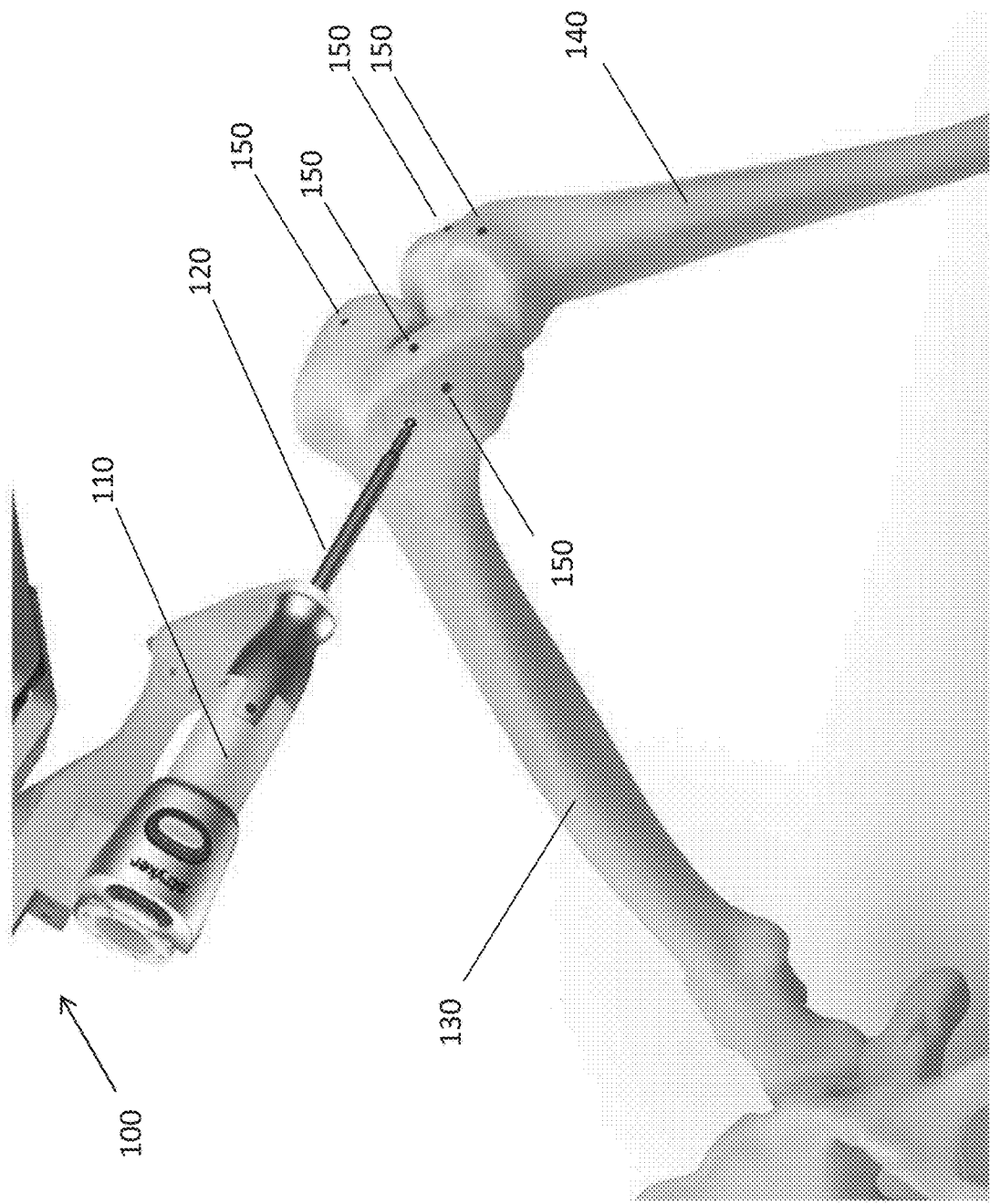
FIG. 1 is a partial perspective view of a robot preparing contingency or bailout holes in a femur and tibia.

An exemplary robotically controlled bone preparation system, or robot 100 for short, that may be used in various joint arthroplasty procedures is illustrated in FIG. 1. Only a portion of the robot 100—an arm 110 and a cutting tool 120—is illustrated in FIG. 1. The robot 100 is shown after having drilled a number of holes 150 into the femur 130 and tibia 140. The holes 150 are referred to herein interchangeably as "contingency" or "bailout" holes, as the holes may only need to be used if the robot 100 fails and the surgeon needs to manually complete the procedure, using the bailout holes 150 as reference points. However, holes 150 may also be interchangeably referred to herein as "plan" points because, as is described in greater detail below, the bailout holes or plan points 150 may be useful in situations other than after failure of the robot 100. Moreover, such plan points 150 may include varying trajectories such that each hole has a unique angle with respect to a plane of a joint. For example, each hole may have a unique (x, y, z) coordinate as an origin point located on the articular surface of a joint, while the hole also includes a unique (x', y', z') coordinate where it terminates in bone. Each hole therefore has a central axis, in which the central axes of the holes may be parallel or not parallel to one another. Therefore, the holes generally have a unique position on the articular surface of bone, the position defining a location and orientation. Because of the general manner in which the holes are produced, the holes are generally cylindrically shaped along their length. The diameter and length or depth of the holes may vary as well depending on the desired dimensions of the pins or posts that may be coupled to the holes if required. Further still, as explained in more detail below, such holes may be used in procedures on other joints, including ball-and-socket joints, such as the shoulder or hip. As illustrated in FIG. 1, the robot 100 is in the process of drilling plan points 150 in preparation for a total knee arthroplasty ("TKA") procedure in which a J-block resection guide is to be used. As is described in greater below, other configurations of plan points 150 may be used for other procedures and for other instruments.

Without limiting the surgical planning described herein to a particular joint or a particular procedure for a joint, there are a number of exemplary joint procedures that may be performed with surgical plan options geared toward manual completion of the procedure. For example, a number of knee procedures may be planned with options or contingencies to the same or alternate knee procedures. For a partial knee replacement ("PKR") different surgical plans may facilitate a surgeon completing the procedure manually as a PKR, or transitioning to a TKA procedure, if such a transition to manual surgery is desired or required. Similarly, a patellofemoral joint ("PFJ") procedure may include different surgical plans that facilitate a surgeon completing the procedure manually as a PFJ, or transitioning to a TKA procedure, if such a transition to manual surgery is desired or required. A PFJ-PKR procedure may include a surgical plan to facilitate a surgeon completing the procedure as a TKA. Similarly, a TKA procedure may include a surgical plan that facilitates a surgeon completing the procedure as a TKA. The intended procedure and the desired contingency procedure influence the particular configuration of holes prepared during the procedure, as does the particular jigs, resection guides or other instruments intended to be used to complete the contingency procedure, both of which are described in greater detail below. For knee procedures, contingency plans may be applicable, for example, to bi-cruciate retaining procedures, posterior-cruciate retaining procedures, and cruciate sacrificing procedures. Table 1 below lists a number of exemplary contingency procedures for different intended procedures that may be possible for knee joints. It should be noted that the list is non-exhaustive and other combinations of intended and contingency procedures, such as BCR to TKA or BCR to BCR, are contemplated within the scope of the disclosure.

TABLE 1

| | Intended Procedure | Contingency Procedure |
|---|---|---|
| Uni-compartmental | PKR | PKR |
| | | TKA |
| | PFJ | PFJ |
| | | TKA |
| Bi-compartmental | PFJ-PKR | TKA |
| Tri-compartmental | TKA | TKA |

Figure 2A:
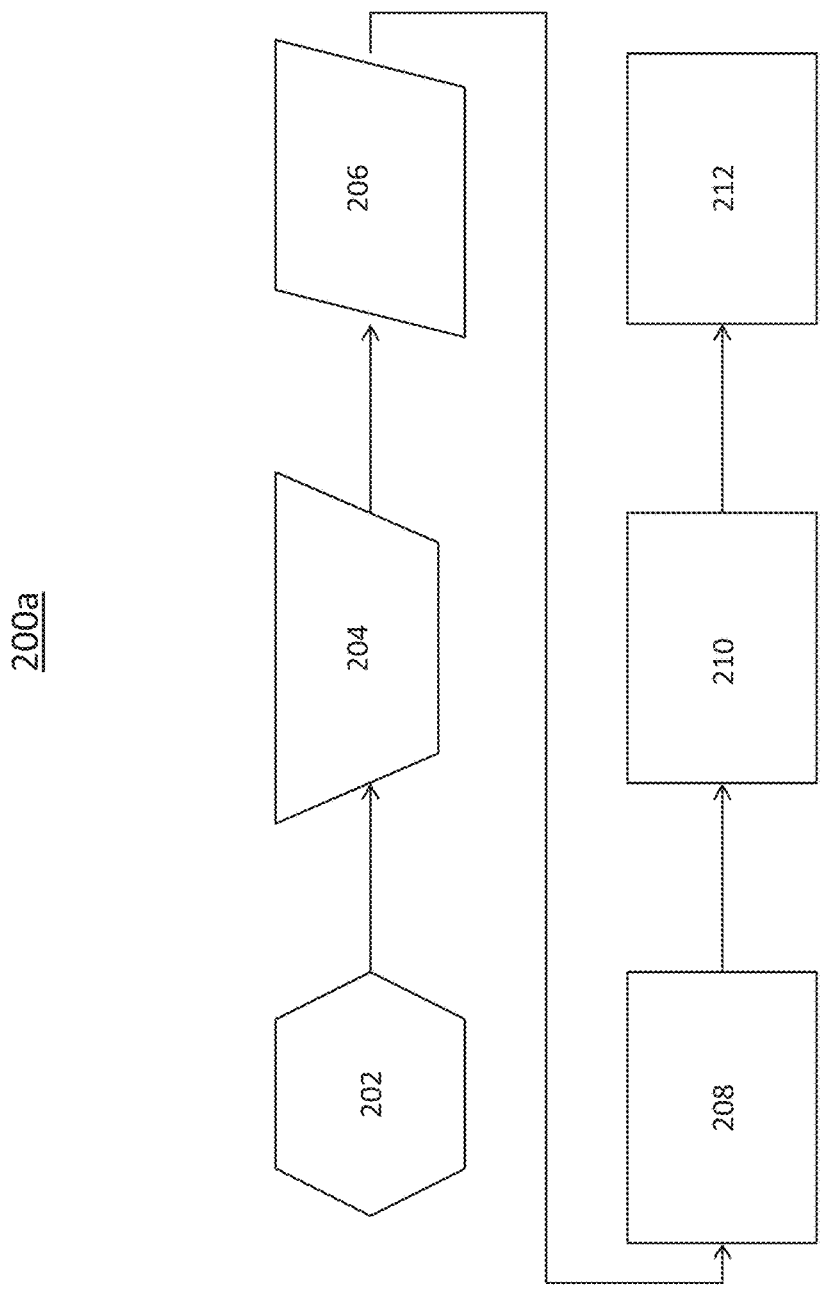
FIG. 2A is a flow chart representing steps of a contingency planning phase in a TKA procedure with a TKA contingency plan.
Figure 2B:
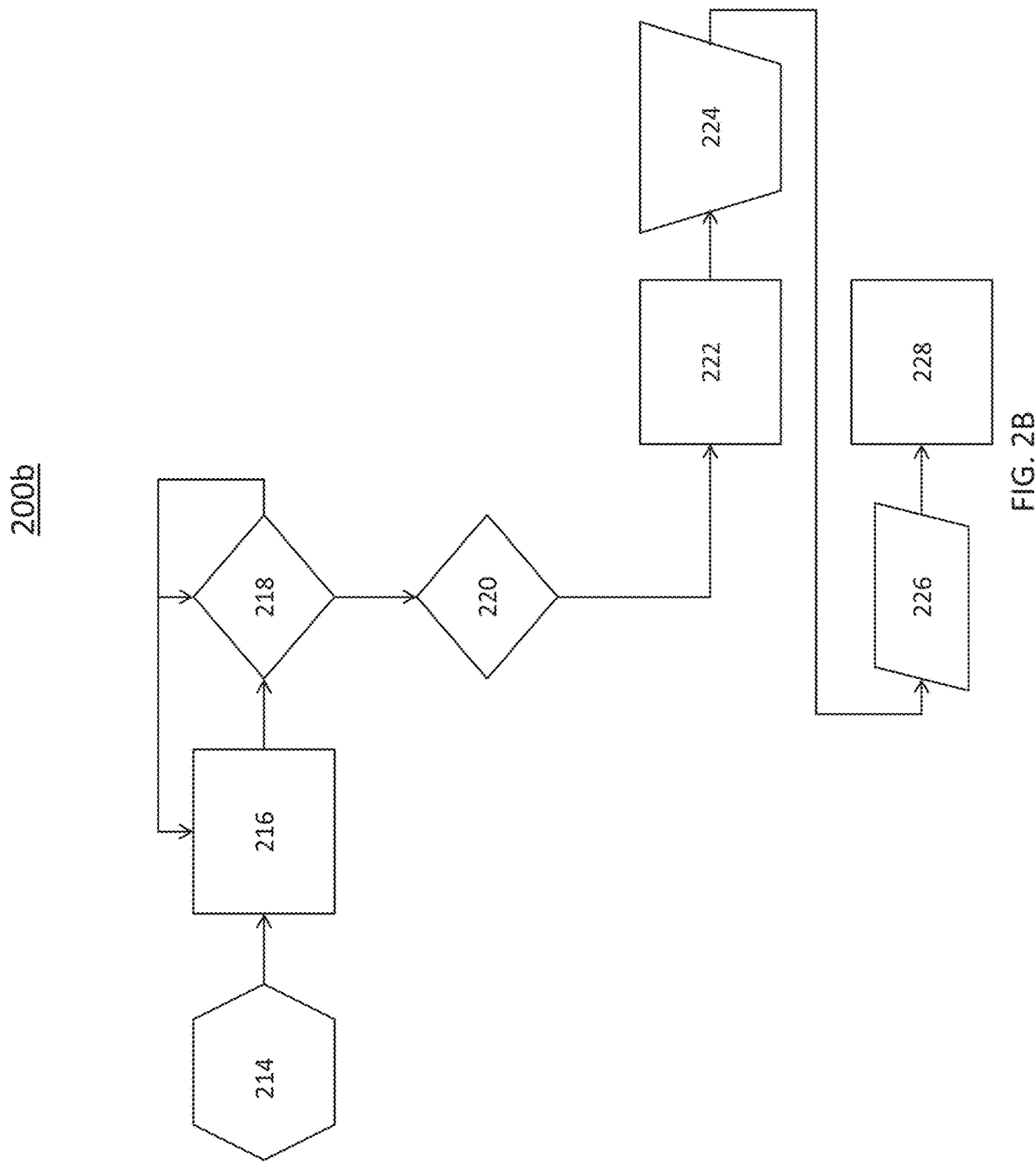
FIG. 2B is a flow chart representing steps of a debulking phase in a robotic TKA procedure.
Figure 2C:
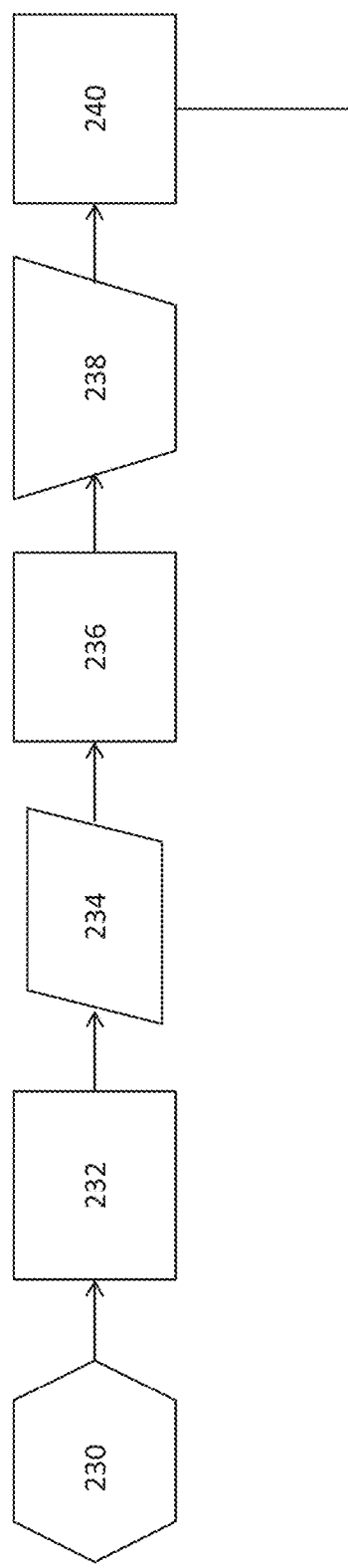
FIG. 2C is a flow chart representing steps of a finishing pass phase in a robotic TKA procedure.
Figure 2C:
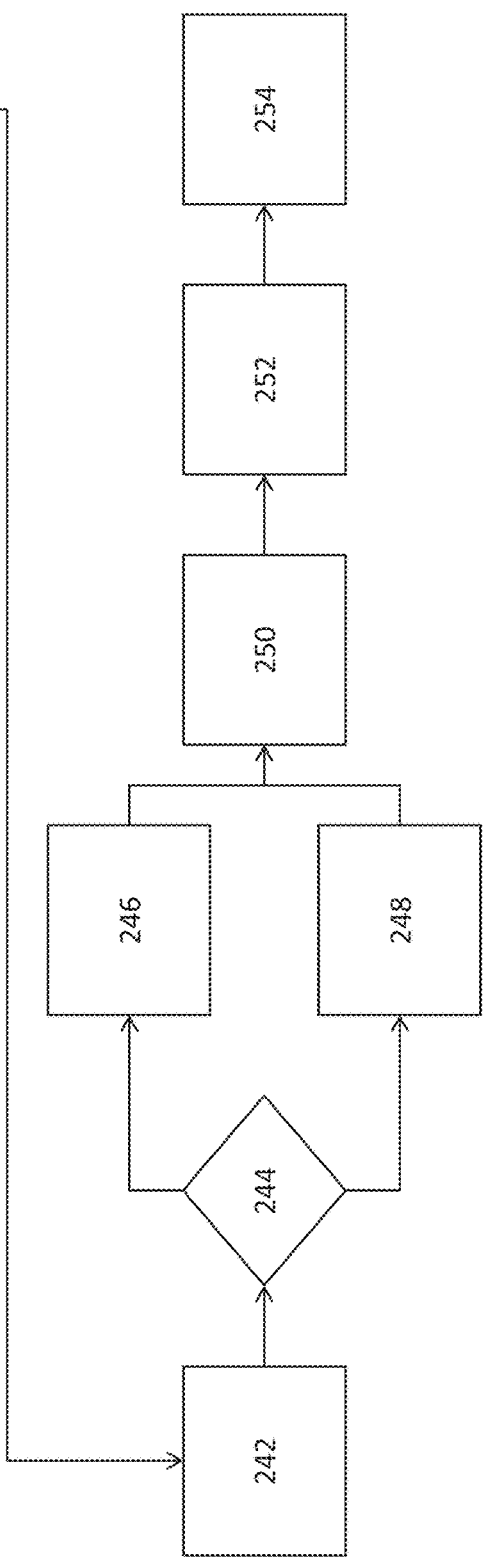

Steps of a TKA procedure such as in cruciate retaining or posterior stabilized procedures, for example, are illustrated in flow charts in FIGS. 2A-C. Specifically FIG. 2A shows a contingency preparation phase 200a, FIG. 2B shows a debulking phase 200b, and FIG. 2C shows a finishing phase 200c. In this particular example, the contingency procedure—a TKA procedure—is the same as the intended procedure.

The particular contingency preparation phase 200a illustrated in FIG. 2A takes the form of creating plan points 150. Specifically, the contingency preparation phase 200a begins with step 202, which includes loading a cutting tool 120, such as a burr or router, on the robot 100. In one example, the cutting tool 120 may be a 2.5 mm burr or router, but other sizes, such as approximately ⅛ inch or approximately 3.175 mm, and other cutting tools may be appropriate. In step 204, the knee is put into flexion, and retractors are positioned in the surgical site to protect the anterior cruciate ligament ("ACL") and posterior cruciate ligament ("PCL"), for example. In step 206, registration is performed with tracker pins, for example. Generally, with registration, the positions of anatomical landmarks and axes are digitized as reference for the alignment of instruments, bone cuts, and the leg. Registration may be performed on the femur 130 and tibia 140 using trackers 540 (see FIGS. 4J-K) that are fixed to the bone to allow the NAV system to guide the robot 100. As part of the registration, for example, the surgeon may touch off key anatomical landmarks, for example, by using a pointer tool of the NAV system to mark the medial and lateral epicondyles such that the NAV system is able to track the location of the key anatomical landmarks during the procedure. The surgeon may then verify the registration, for example, by reviewing and confirming the digitized mechanical axes and analyzing initial leg alignment with respect to range of motion, varus/valgus misalignment and laxity, and flexion contracture or hyperextension. Once verified, the surgeon may accept the surgical plan in step 208.

Figure 2E:
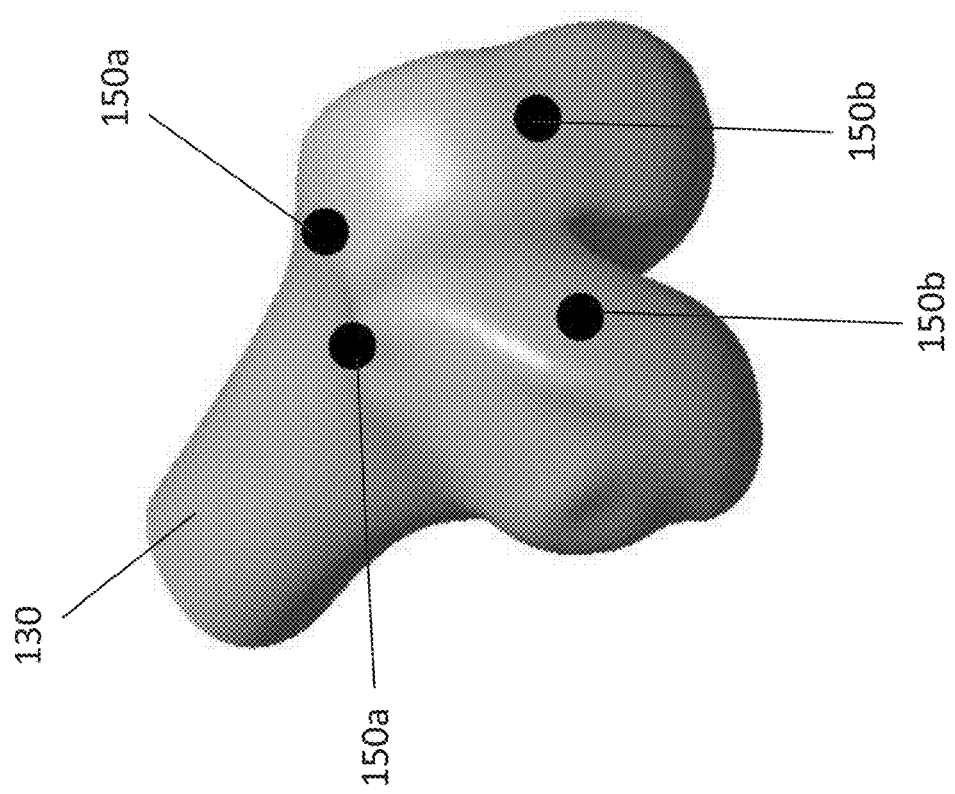
FIG. 2E is a partial perspective view of an alternate configuration of bailout holes created in a femur in the contingency planning phase of FIG. 2A.
Figure 2D:
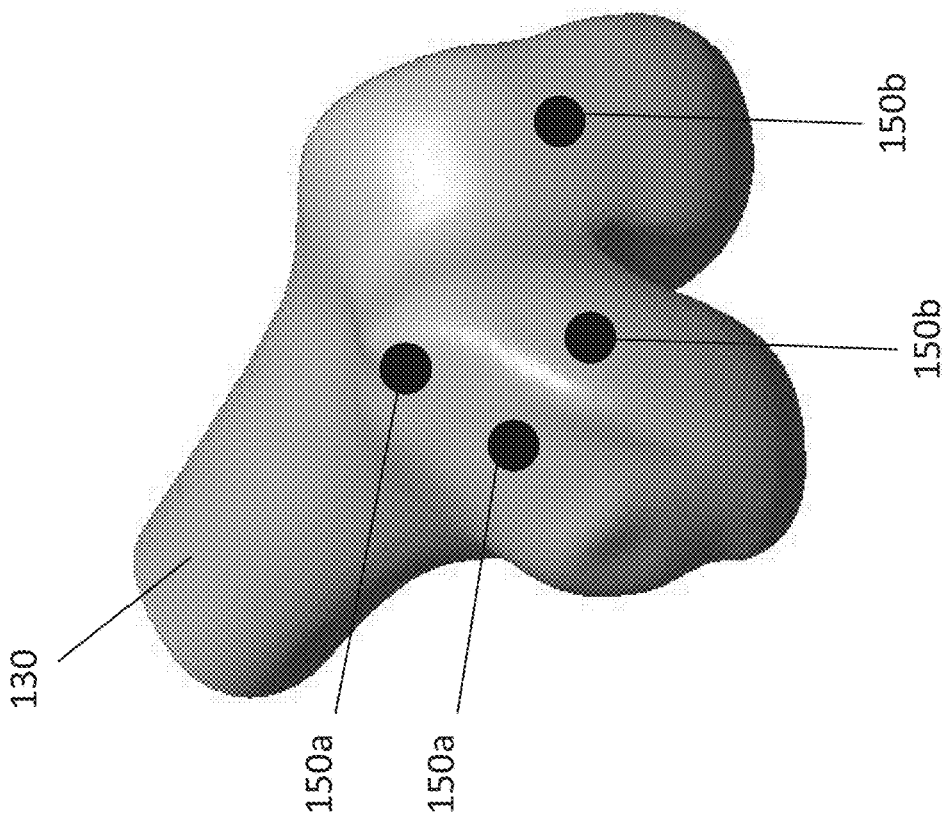
FIG. 2D is a partial perspective view of an exemplary configuration of bailout holes created in a femur in the contingency planning phase of FIG. 2A.
Figure 2F:
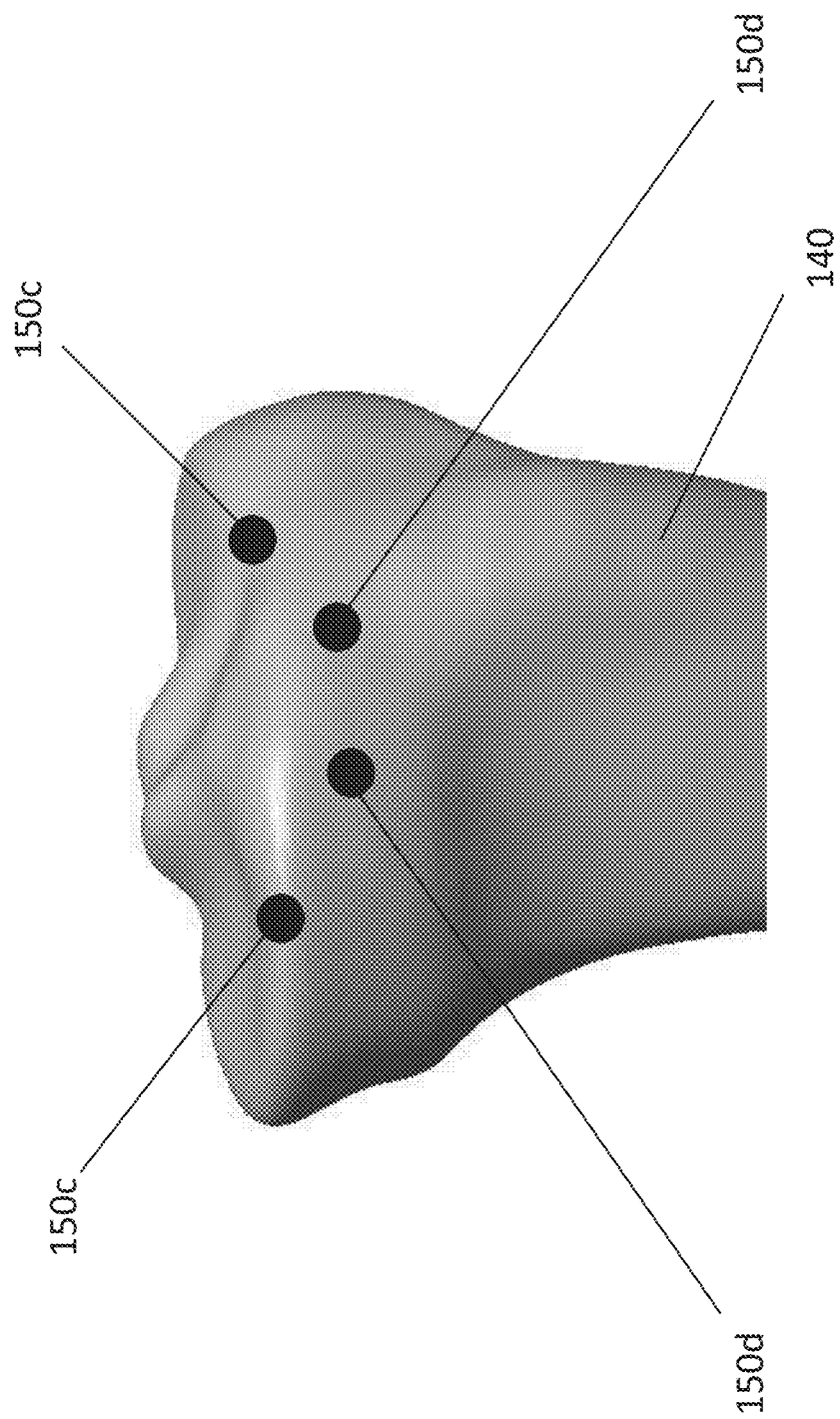
FIG. 2F is a partial perspective view of an exemplary configuration of bailout holes created in a tibia in the contingency planning phase of FIG. 2A.

The robot 100 drills four plain points 150, for example, into the femur 130 in step 210. As described above, in addition to the intended and the contingency procedure, the number and position of the plan points 150 may also depend on the particular instruments intended for use with the procedure. For example, a different configuration of plan points 150 may be used if a femoral resection is to be guided by a J-block resection guide, a universal resection guide, a navigated MIS guide, or any other suitable guide. As illustrated in FIG. 2D, the four plan points 150 in the femur 130 may include two anterolateral plan points 150a and two distal plan points 150b. In another embodiment, step 210 may entail drilling two anterior plan points 150a and two distal plan points 150b as illustrated in FIG. 2E. In step 212, the robot 100 may drill four plan points 150 into the tibia 140. Specifically, as illustrated in FIG. 2F, the plan points 150 may include two proximal plan points 150c. Step 212 may also include the robot 100 drilling two proximal-anterior plan points 150d in the tibia 150. Although it is preferred for the robot 100 to create the plan points 150, it is contemplated that the plan points 150 may be created manually for all the surgical plans described herein.

Figure 2H:
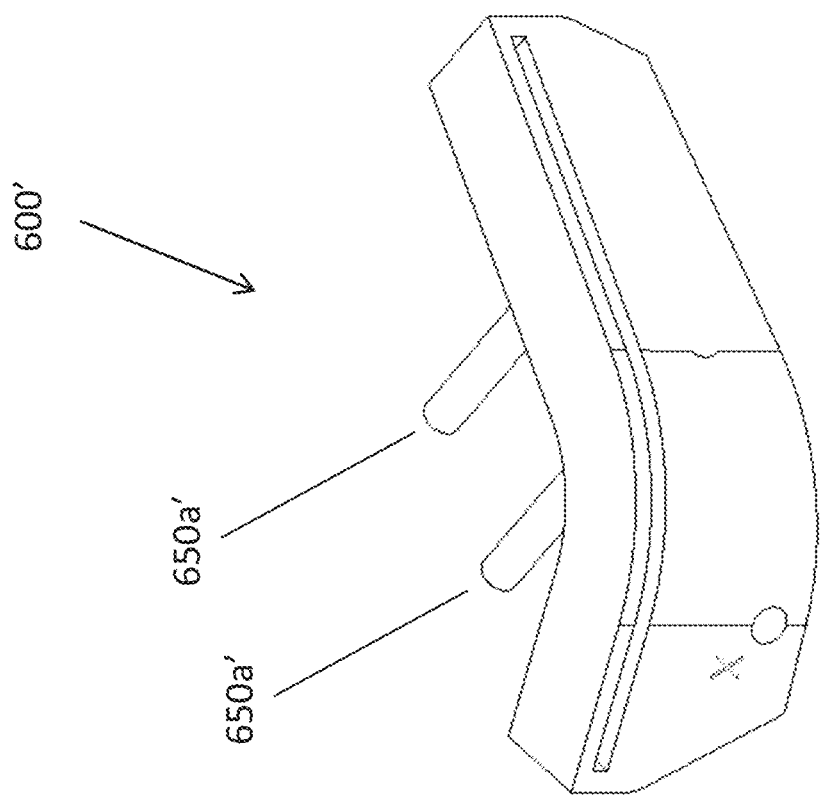
FIG. 2H is a perspective view of an alternate embodiment of a monolithic J-block resection guide.
Figure 2G:
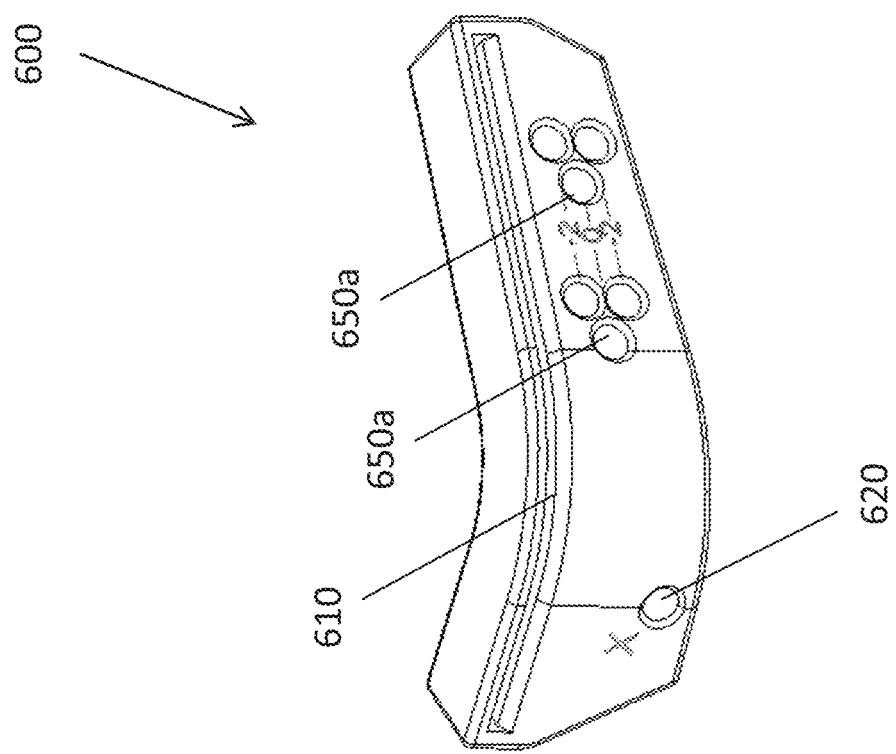
FIG. 2G is a perspective view of a J-block resection guide.
Figure 2J:
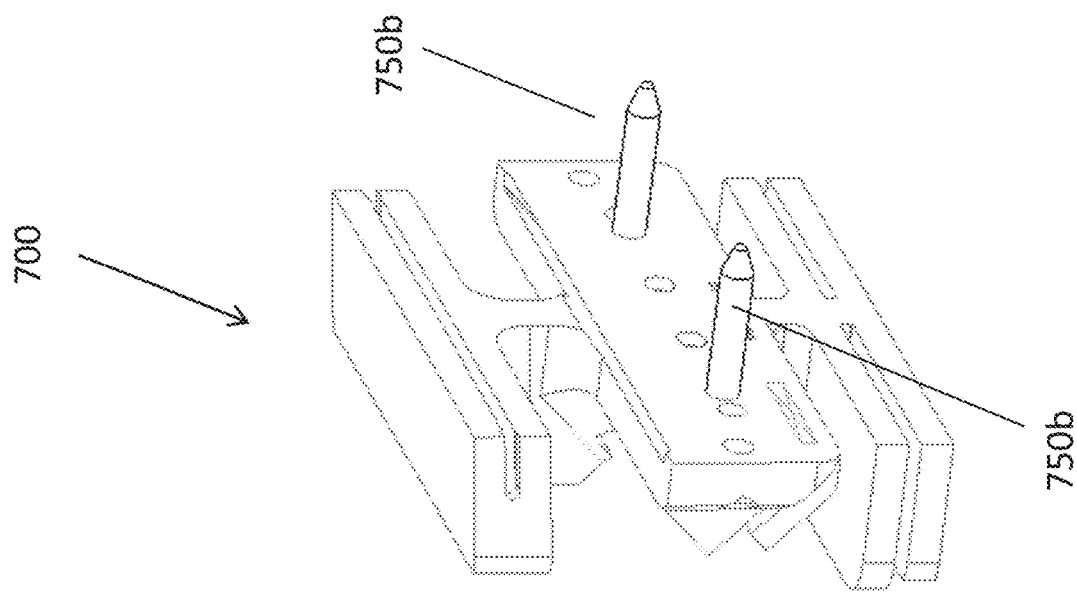
FIG. 2J is a rear perspective view of the 4-in-1 cutting guide of FIG. 2I.
Figure 2I:
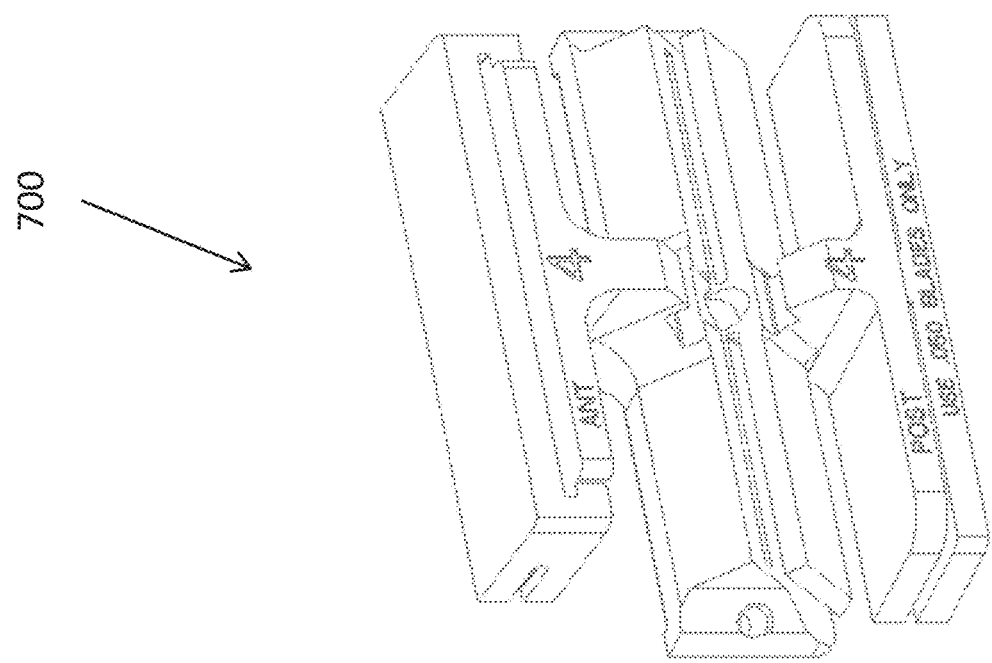
FIG. 2I is a front perspective view of a 4-in-1 cutting guide.
Figure 2K:
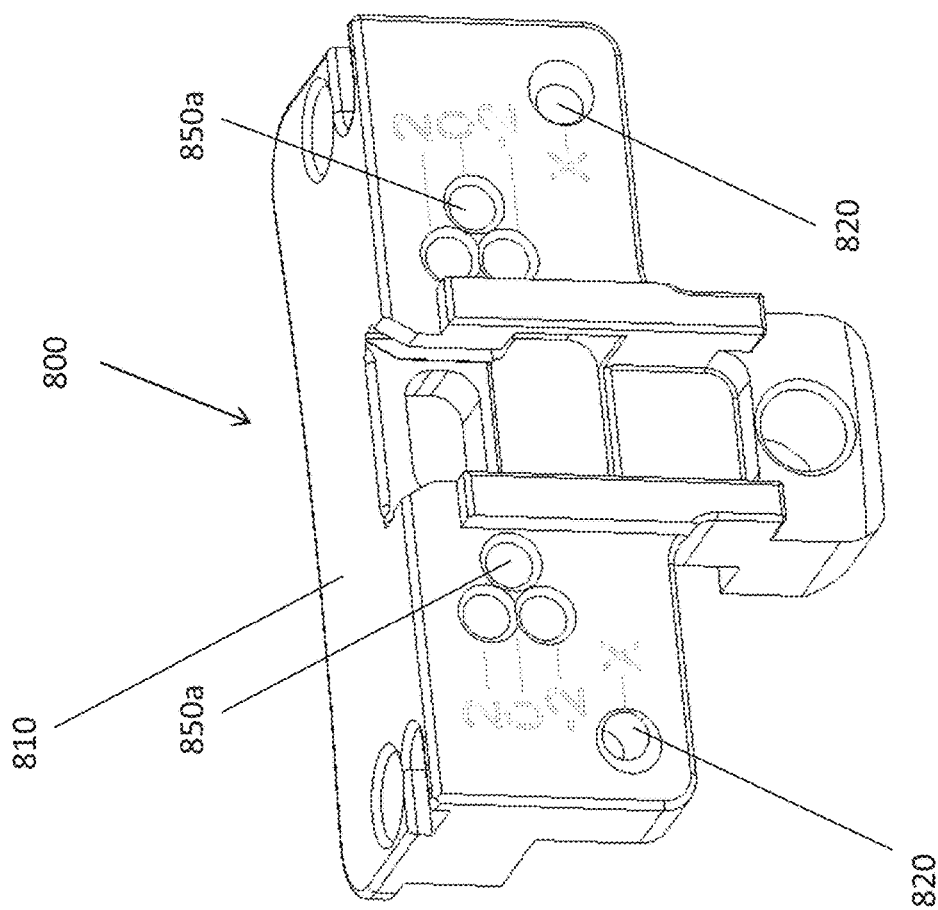
FIG. 2K is a perspective view of a universal resection guide.

The plan points 150 may provide references for the surgeon to use if the robot 100 should fail later in the procedure, or to otherwise aid a surgeon in manually completing a procedure. For example, in the configuration illustrated in FIG. 2D, the two anterolateral plan points 150a may be configured to align with guide holes 650a in a J-block resection guide 600 as illustrated in FIG. 2G. Fixation pins may be placed through each of a pair of guide holes 650a and further into plan points 150a to fix the J-block 600 to the bone. J-block resection guide 600 may be generally "J"-shaped and include a number of sets or pairs of guide holes, each set being a different distance from a cutting slot 610. J-block resection guide 600 may also include additional holes, such as cross-pin hole 620, to provide additional stability when fixing the resection guide to the bone. An alternate monolithic J-block 600' as illustrated in FIG. 2H, may be used instead of J-block 600. Rather than having pairs or sets of holes 650a, J-block 600' has a pair of posts 650a' that are configured to be inserted into plan points 150a. The two distal femoral plan points 150b may be sized and configured to mate with a 4-in-1 cutting block 700, as illustrated in FIGS. 2I-J and as is known in the art. In particular, posts 750b may be used to attach the 4-in-1 cutting block 700 to the femur 130.

Figure 2L:
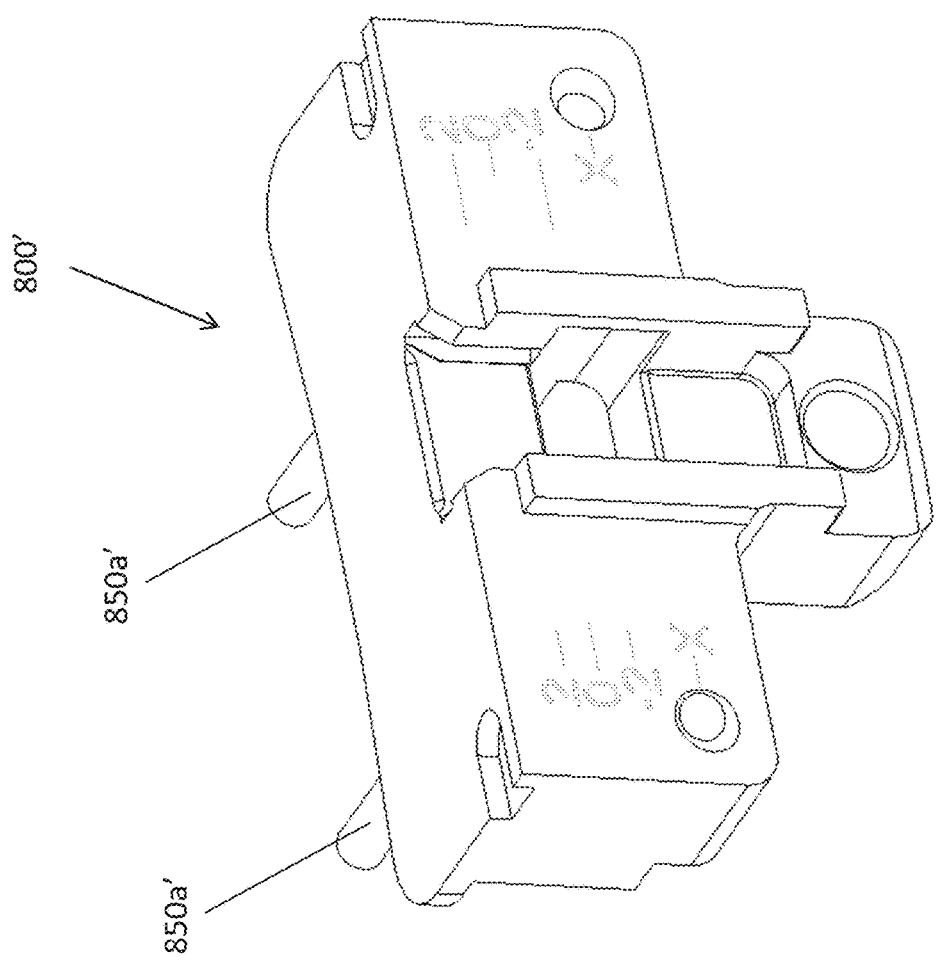
FIG. 2L is a perspective view of an alternate embodiment of a monolithic universal resection guide.

The configuration of plan points 150 illustrated in FIG. 2E may be configured to align with guide holes 850a in a universal resection guide 800, as illustrated in FIG. 8K. Fixation pins may be placed through each of a pair of guide holes 850a and further into plan points 150a to fix the universal resection guide 800 to the bone. Universal resection guide 800 may include a number of sets or pairs of guide holes 850a, each set being a different distance from a top surface 810. Universal resection guide 800 may also include additional holes, such as cross-pin holes 820, to provide additional stability when fixing the resection guide to the bone. An alternate monolithic universal resection guide 800' as illustrated in FIG. 2L, may be used instead of universal resection guide 800. Rather than having pairs or sets of holes 850a, universal resection guide 800' has a pair of posts 850a' that are configured to be inserted into plan points 150a. As in the previous embodiment, the two distal femoral plan points 150b may be sized and configured to mate with 4-in-1 cutting block 700.

Referring again to FIG. 2F, the two proximal-anterior tibial plan points 150d may be sized and positioned to mate with a proximal tibial resection guide to facilitate the proximal tibial cut. The two proximal tibial plan points 150c, which may be optional, may be sized and shaped to mate with a tibial template for rotation assessment and trial reduction.

The remaining steps in the cruciate retaining or posterior stabilized TKA procedure are described immediately below according to a successful procedure in which the robot 100 completes the procedure. In the debulking phase 200b, illustrated in FIG. 2B, the first step 214 is to load (or switch to) a cutting tool, such as a barrel burr, onto the robot 100. The cutting tool may be, for example, a 6, 8, or 10 mm barrel burr. However, other sizes and other cutting tools may also be appropriate. In step 216, the posterior and distal femur 130 are debulked with chamfer cuts and the proximal tibia is debulked. The debulking may be done simultaneously or sequentially. Tissue balancing may be done in step 218 if required. If not required, the surgeon may move to the baseplate step 220. If required, the surgeon may perform tissue or ligament balancing as is known in the art. For example, the surgeon may check the tensioning of the knee in flexion and extension, and check the alignment of the mechanical axis using a manual distractor and/or the graphic user interface of the NAV system. If the intraoperative measurements are acceptable, the surgeon may move to the baseplate step 220. If they are not acceptable, the surgeon may perform soft tissue release. Following the soft tissue release, the surgeon may repeat step 218 for other degrees of freedom of the knee. Alternately, if additional bone surface preparation is required, the surgeon may return to the debulking step 216 after performing the tissue release. Once the surgeon is satisfied with the tissue balancing step 218, he may advance to the baseplate step 220.

From the baseplate step 220, the surgeon may check and verify rotation using a tibial template in step 222. Depending on the type of baseplate being used, the tibia 140 may need to be further prepared prior to approving rotation. For example, if a universal baseplate is to be used, the surgeon may debulk the tibia for accepting the universal stem of the baseplate. Alternatively, if a primary baseplate is to be used, the surgeon may move directly from baseplate step 220 to step 222 to approve rotation using a tibial template. Once rotation is approved, the knee is placed in extension in step 224 and retractors and a patella clamp are positioned in the surgical site as necessary and as is known in the art. In step 226, the surgeon removes the tibial tracker 540 and attached the patella clamp with its associated tracker and performs registration for the NAV system, as is also known in the art. Finally, in step 228, the patella is debulked, bringing the debulking phase 200b to an end.

In the first step 230 of the finishing pass phase 200c, as illustrated in FIG. 2C, a cutting tool, such as a finishing router, is loaded onto the robot 100. The router may be, for example, a 2.5 mm router, but other sizes and other cutting tools may be appropriate. In step 232, the patella is finished by the robot, and fixation holes for the pegs in the patellar implant are created in the patella. At this point, in step 234, the patella clamp and tracker 540 are removed and the tibial tracker is turned on. The anterior femoral surface is finished in step 236 with the robot. Alternatively, the anterior femoral surface may be finished earlier with the larger cutting tool.

After the femoral surface is finished, the knee is put into flexion in step 238 and retractors are positioned in the surgical site. Once in position, in step 240, the distal/posterior femur and proximal tibia are posed in flexion, between approximately 90 and approximately 110 degrees. Femoral preparation is completed, including, for example, preparing the "box" for posterior stabilized TKA procedures. Next, in step 242, the tibial insert thickness is selected using the tibial template. Once selected, the tibial keel is prepared in step 244. The tibial keel may be, for example, prepared at full depth in step 246 if cement is used, or at partial depth in step 248 if the implantation will be cementless. One the tibial keel is prepared, the surgeon may complete the procedure by trialing the implant components in step 250 to verify proper size and position, create the femoral pegs using the robot 100 in step 252, and implanting the components in step 254.

In the procedure described above for cruciate retaining or posterior stabilized TKA, if the robot 100 and NAV system fail during the procedure after the robot has entered the debulking phase 200b, the surgeon may continue the procedure manually using the plan points (or bailout holes) 150. Specifically, depending on the configuration of plan points 150 prepared, the surgeon may attach a distal femoral resection guide to the femur. For example, with reference to FIG. 2D, the surgeon may attach a J-block resection guide 600 or 600' to the femur 130 using anterolateral femoral plan points 150a. This or a similar configuration of plan points 150 may also allow use of a navigated MIS jig 500, illustrated in FIGS. 4F-K. Alternately, with reference to FIG. 2E, the surgeon may attach a universal resection guide 800 or 800' to the femur 130 using anterior plan points 150a. Once attached, the surgeon may make the femoral distal cut using the guide. Referring to FIGS. 2D-E, following the femoral distal cut, the surgeon may attach, for example, a 4-in-1 cutting block 700 to the femur using the distal femoral plan points 150b. Once attached, the surgeon may make additional femoral cuts including, for example, an anterior cut, a posterior cut, and anterior and posterior chamfer cuts using the aforementioned 4-in-1 guide 700. Similarly, the surgeon may attach a tibial resection guide to the tibia 140 using the proximal-anterior tibial plan points 150*d*. Finally, the tibial template may be attached to the tibia 140 using proximal tibial plan points 150*c* for rotation assessment and trial reduction. A number of intermediate steps to those described directly above are not explicitly detailed here, as they may be similar to those described above with relation to the complete successful robotic procedure, or are otherwise known in the art. Because the plan points 150 are created to correspond to traditional components used in manual TKA procedures, a surgeon will be able to relatively seamlessly transition from a robotic TKA procedure to a manual TKA procedure in the case the robot 100 fails.

In fact, the robot 100 may even be used to create the plan points 150 when the surgeon intends to perform a manual TKA procedure and has no intention to use the robot 100 after the plan points 150 are created. For example, a surgeon may prefer to have the robot 100 pre-drill the plan points 150, which would be used not as "bailout" holes in case a contingency plan needs implementation, but rather in a case in which a manual procedure is intended after the robot pre-drills the holes. This may be preferred, for example, because the plan points 150 made by the robot 100 may provide a way to set up highly accurate cuts using a jig, such as the J-block or universal resection guides 600 (or 600'), 800 (or 800'). Further, the use of the robot 100 to implement these plan points 150 may allow a predetermined surgical plan to be used to determine the location of the holes and thus the positioning of the jigs and ultimately the precise location of the cuts. And this is not limited to drilling holes. For example, robot 100 may machine the bone to have any number of features that correspond to a surgical instrument or implant. For example, the robot 100 may machine the bone to have a precisely curved surface to correspond to a curved surface of an implant. Machining such a curved surface without the use of a robot may be impossible to accurately reproduce by hand. For example, the robot 100 may machine the curved surface such that the machined surface of the bone corresponds to an axis of rotation of an implant to be implanted onto the bone. Once the surface is machined by the robot 100, the user may manually complete the procedure by attaching the implant to the bone and performing any additional required steps. Still further, the robot 100 may create curved holes in the bone to accept, for example, a curved keel of a prosthetic implant. It may only be possible to accurately reproduce such a curved hole that corresponds to a curved structure of an implant via the robot 100, which may be impossible to create manually. In each of the above examples, the machining by the robot 100 is not used strictly as a contingency plan. Rather, the robot 100 is being used to provide a benefit of robotic machining including, for example accuracy, speed, and/or reproducibility. Despite use of the robot 100, the intent from the outset is to manually complete the procedure without further use of the robot 100 after the initial machining of the bone by the robot 100.

Plan points 150 may also provide other benefits, such as confirming or rescuing registration. As noted above in connection with step 206 of FIG. 2A, a user may perform registration to digitize the positions of anatomical landmarks and axes as reference for the alignment of instruments, bone cuts, and the leg. Subsequent to registration, a user may reference plan points 150 to check the accuracy of registration and also to rescue a compromised registration, for example in the event a tracker 540 has been moved inadvertently. To accomplish this, the user may place the pointer tool in the desired plan point 150 and visualize the location of the hole and pointer tool on the NAV screen as it relates to the physical anatomy in situ. If the screen image does not match the tangible anatomy under direct visualization the user may determine that the tracker 540 likely moved subsequent to the step of verifying the registration. The user may then direct the guidance system to calculate the difference between the altered tracker location and/or coordinate system and the previous registration, and adjust accordingly so that the altered tracker location and/or coordinate system can be used to complete the procedure successfully. After the calculations are completed and the coordinate systems are adjusted, the procedure can be completed as planned. The above described procedure of registration verification, as well as registration rescue, may apply with equal force to the other specific surgical plans described herein.

Figure 3A:
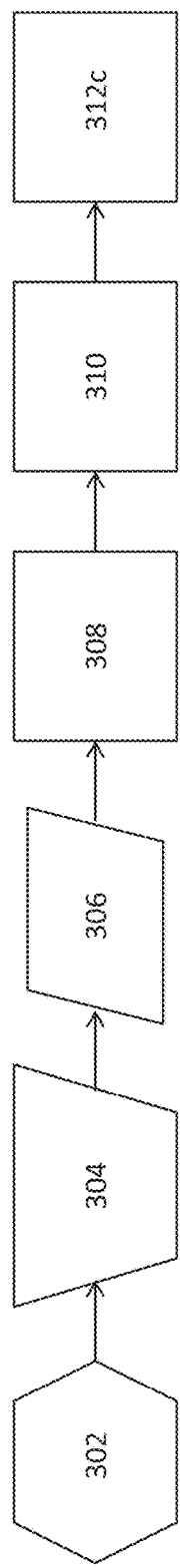
FIG. 3A is a flow chart representing steps of a contingency planning phase in a bicruciate retaining ("BCR") procedure with a TKA contingency plan.
Figure 3B:
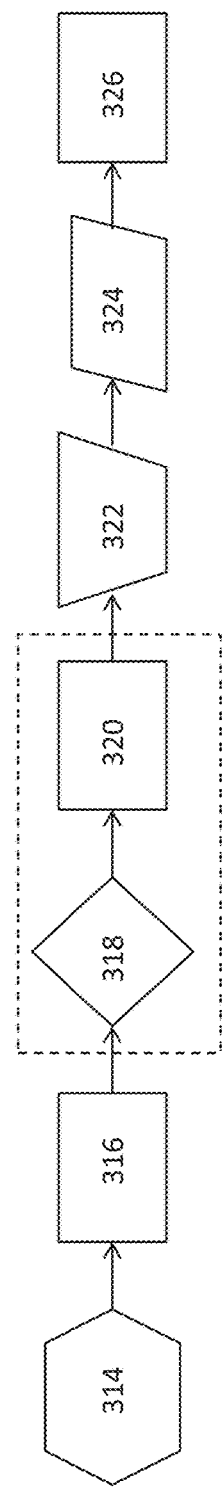
FIG. 3B is a flow chart representing steps of a debulking phase in a robotic BCR procedure.
Figure 3C:
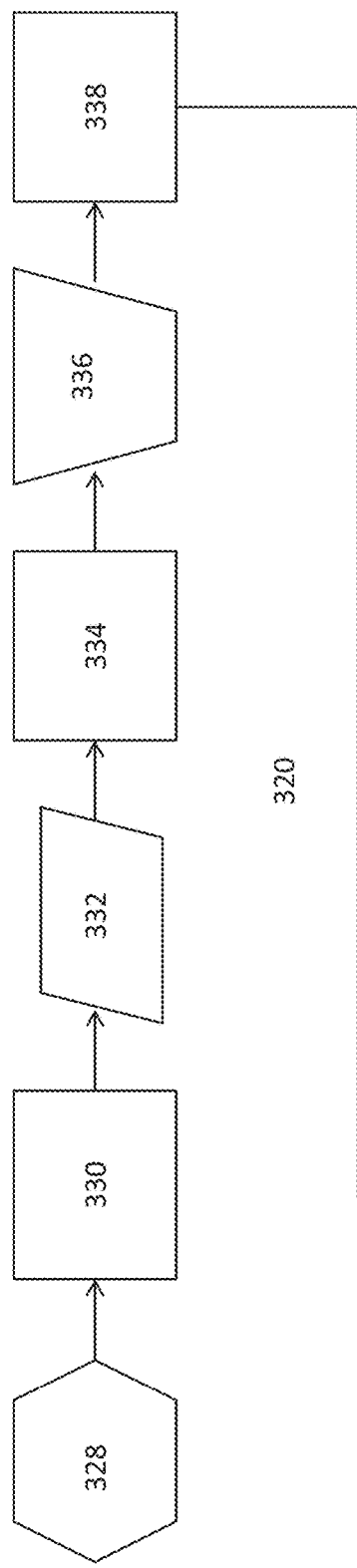
FIG. 3C is a flow chart representing steps of a finishing pass phase in a robotic BCR procedure.
Figure 3C:
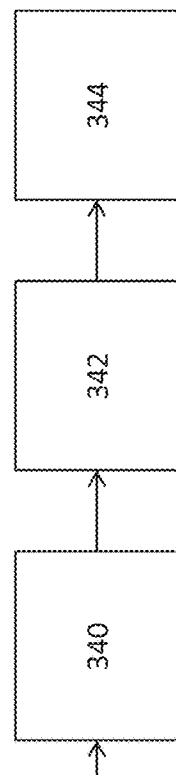

Steps of a BCR procedure with a contingency plan of a TKA procedure are illustrated in flow charts in FIGS. 3A-C. Specifically FIG. 3A shows a contingency preparation phase 300*a*, FIG. 3B shows a debulking phase 300*b*, and FIG. 3C shows a finishing phase 300*c*.

Figure 3D:
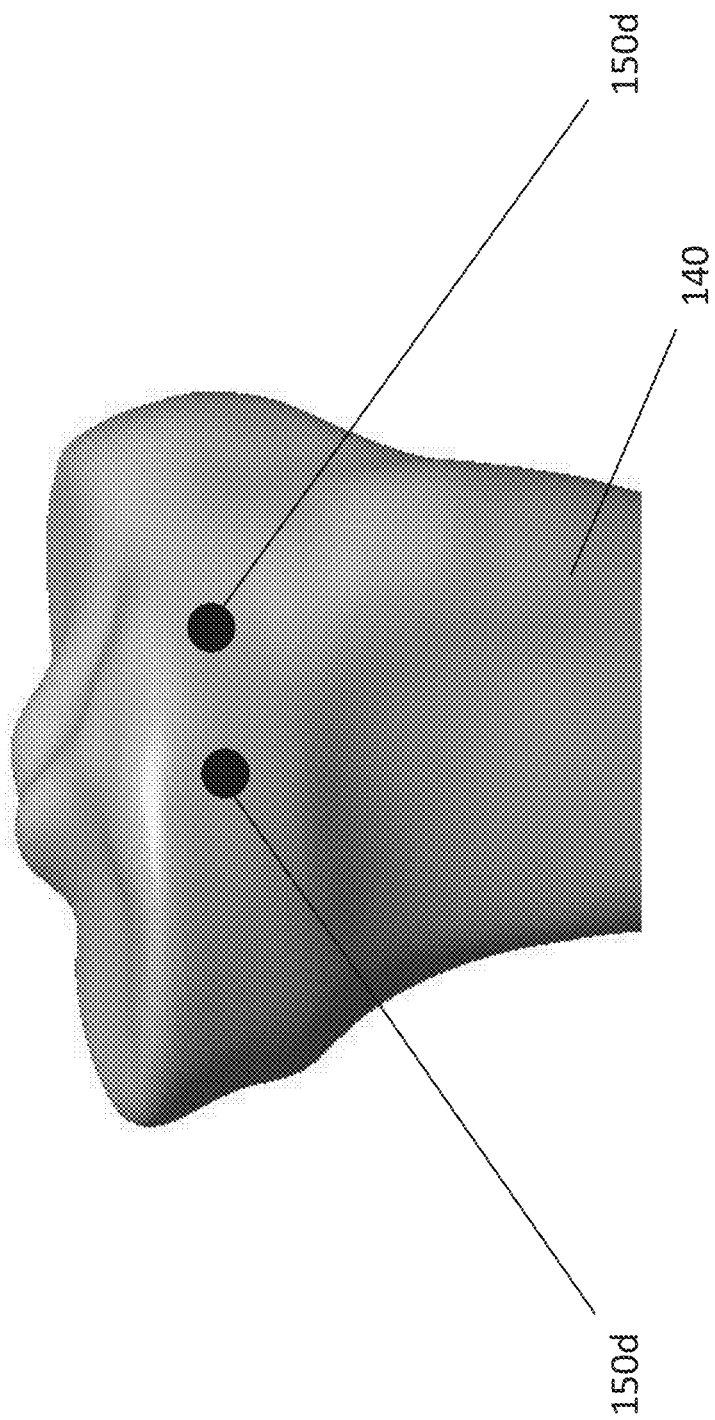
FIG. 3D is a partial perspective view of bailout holes created in a tibia in the contingency planning phase of FIG. 3A.

The particular contingency preparation phase 300*a* illustrated in FIG. 3A takes the form of creating plan points 150. The configuration of the femoral plan points 150 may be, for example, the same as illustrated in FIG. 2D or FIG. 2E, depending on the particular instrumentation desired for use. The configuration of the tibial plan points 150 may be, for example, the same as illustrated in FIG. 2F or may take the configuration illustrated in FIG. 3D. Specifically, the contingency preparation phase 300*a* begins with step 302, which includes loading a cutting tool 120, such as a router, on the robot 100. In one example, the cutting tool 120 may be a 2.5 mm router, but other sizes, such as approximately ⅛ inch or approximately 3.175 mm, and other cutting tools may be appropriate. In step 304, the knee is put into flexion, and retractors are positioned in the surgical site to protect the ACL and PCL. In step 306, registration is performed using femur 130 and tibia 140 trackers 540 to allow the NAV system to guide the robot 100. The surgeon may accept the surgical plan in step 308 if satisfied, touching off key landmarks and verifying placement.

The robot 100 drills four plan points 150 into the femur 130 in step 310. Specifically, as illustrated in, and described in relation to, FIGS. 2D-E, the four plan points 150 in the femur 130 may include two anterolateral plan points 150*a* and two distal plan points 150*b* (FIG. 2D) or two anterior plan points 150*a* and two distal plan points 150*b* (FIG. 2E). In step 312, the robot 100 may drill two proximal-anterior plan points 150*d* into the tibia 140. Alternately, the robot 100 may drill two proximal-anterior plan points 150*d* and two proximal plan points 150*c* in the tibia 140, as illustrated in, and described in relation to, FIG. 2F.

As described with relation to the contingency preparation phase 200*a* for the posterior stabilized of cruciate retaining TKA procedure, the plan points 150 for the BCR to TKA procedure may provide references for the surgeon to use if the robot 100 should fail later in the procedure and the procedure is to be completed as a TKA, or if the surgeon otherwise decides to complete the procedure manually as a TKA.

The remaining steps in the BCR to TKA procedure are described immediately below according to a successful BCR procedure in which the robot 100 completes the procedure. In the debulking phase 300*b*, illustrated in FIG. 3B, the first step 314 is to load (or switch to) a cutting tool, such as a barrel burr, onto the robot 100. The cutting tool may be, for example, a 6, 8, or 10 mm barrel burr. However, other sizes and other cutting tools may also be appropriate. In step 316, the posterior and distal femur 130 are debulked with chamfer cuts and the proximal tibia is debulked. The debulking may be done simultaneously or sequentially. Tissue balancing may be done in step 318 if required, although balancing may not be recommended in a BCR procedure. Following the tissue balancing step 318, the surgeon may perform an intraoperative assessment of the surgical plan and make changes if necessary in step 320. After step 320, or after step 316 if tissue balancing is not required, the surgeon may put the knee in flexion in step 322, attaching retractors and positioning a patella clamp as necessary. The tibial tracker 540 is turned off in step 324 and the patella clamp with tracker is attached and registered for the NAV system. The robot 100 debulks the patella in step 326, bringing the debulking phase 300b to an end.

In the first step 328 of the finishing pass phase 300c, as illustrated in FIG. 3C, a cutting tool, such as a finishing router, is loaded onto the robot 100. The router may be, for example, a 2.5 mm router, but other sizes and other cutting tools may be appropriate. In step 330, the patella is finished by the robot, and fixation holes for the pegs in the patellar implant are created in the patella. At this point, in step 332, the patella clamp and tracker 540 are removed and the tibial tracker is reattached. The anterior femoral surface is finished in step 334 with the robot.

After the femoral surface is finished, the knee is put into flexion in step 336 and retractors are positioned in the surgical site to protect the ACL and PCL. Once in position, in step 240, the distal/posterior femur and proximal tibia are posed in flexion, between approximately 90 and approximately 110 degrees. In step 338, femoral preparation is completed, including, for example, preparation of femoral pegs. Tibial preparation is also completed step 338, including, for example, preparation of the tibial plateau, the tibial eminence periphery, and the tibial keel. Next, in step 340, the tibial insert thickness is selected using the tibial template, as is known in the art. Once selected, the surgeon may complete the procedure by trialing the implant components in step 342 to verify proper size and position, and implanting the components in step 344.

In the procedure described above for BCR to TKA, if the robot 100 and NAV system fail during the procedure after the robot has entered the debulking phase 300b, the surgeon may continue the procedure manually as a TKA using the plan points as bailout holes 150. This contingency procedure would be essentially the same as described for the TKA to TKA procedure above. It should be noted that the BCR procedure may be planned with plan points 150 such that the contingency procedure is also a BCR procedure. Similar as to what is described above, plan points 150 may be used for completing a procedure manually, even in cases where the robot 100 does not fail and the original plan includes manual completion.

Figure 4A:
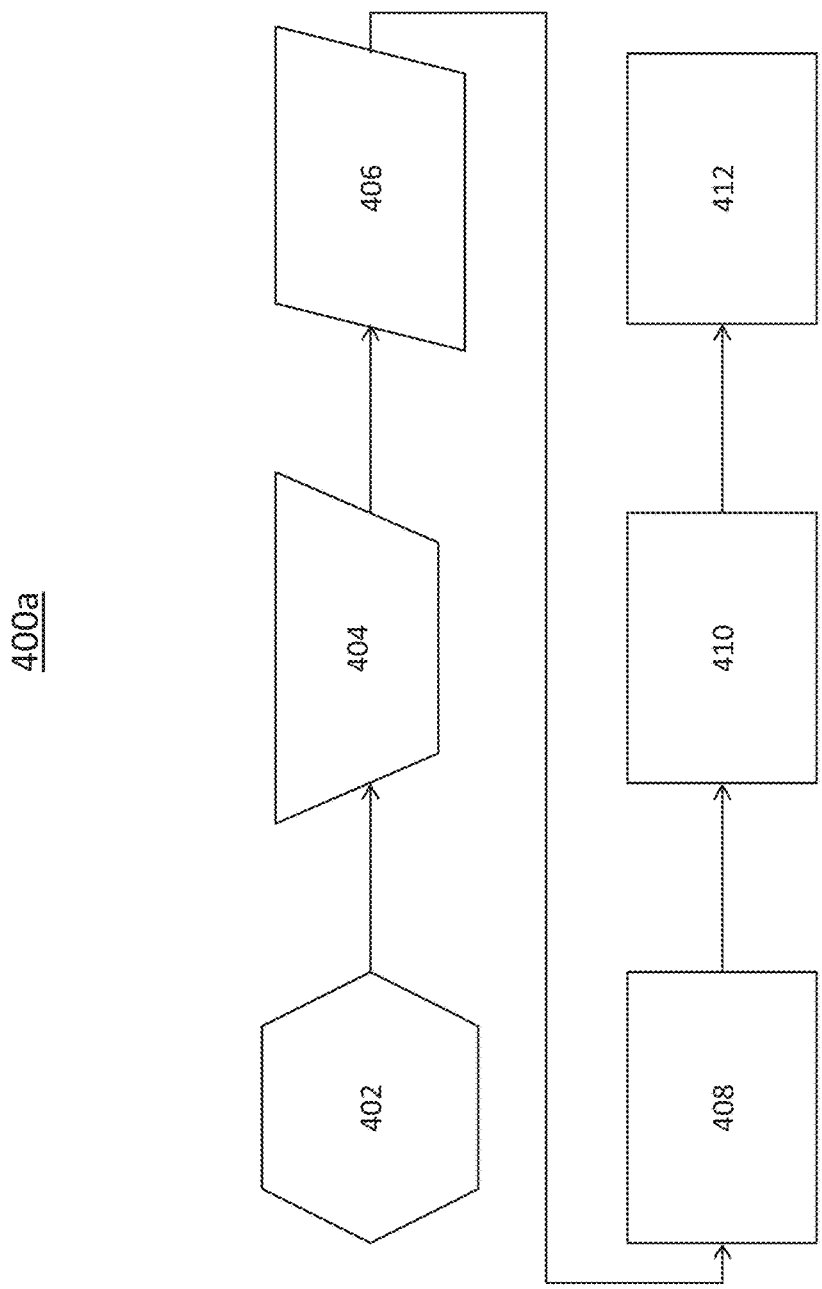
FIG. 4A is a flow chart representing steps of a contingency planning phase in a partial knee replacement ("PKR") procedure with a TKA contingency procedure.
Figure 4B:
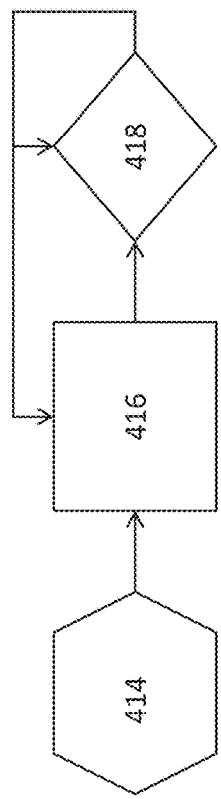
FIG. 4B is a flow chart representing steps of a debulking phase in a robotic PKR procedure.
Figure 4C:
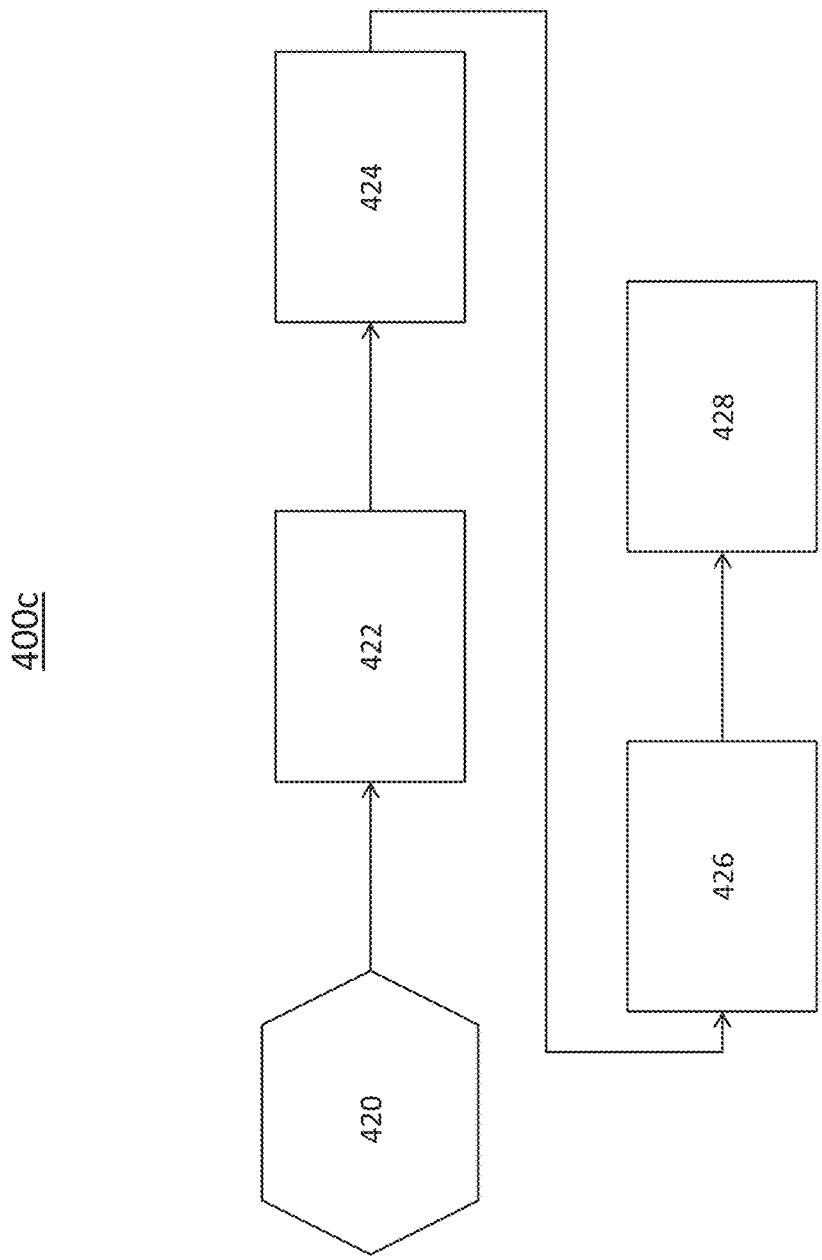
FIG. 4C is a flow chart representing steps of a finishing pass phase in a robotic PKR procedure.

Steps of a PKR procedure are illustrated in flow charts in FIGS. 4A-C. Specifically FIG. 4A shows a contingency preparation phase 400a, FIG. 4B shows a debulking phase 400b, and FIG. 4C shows a finishing phase 400c.

Figure 4E:
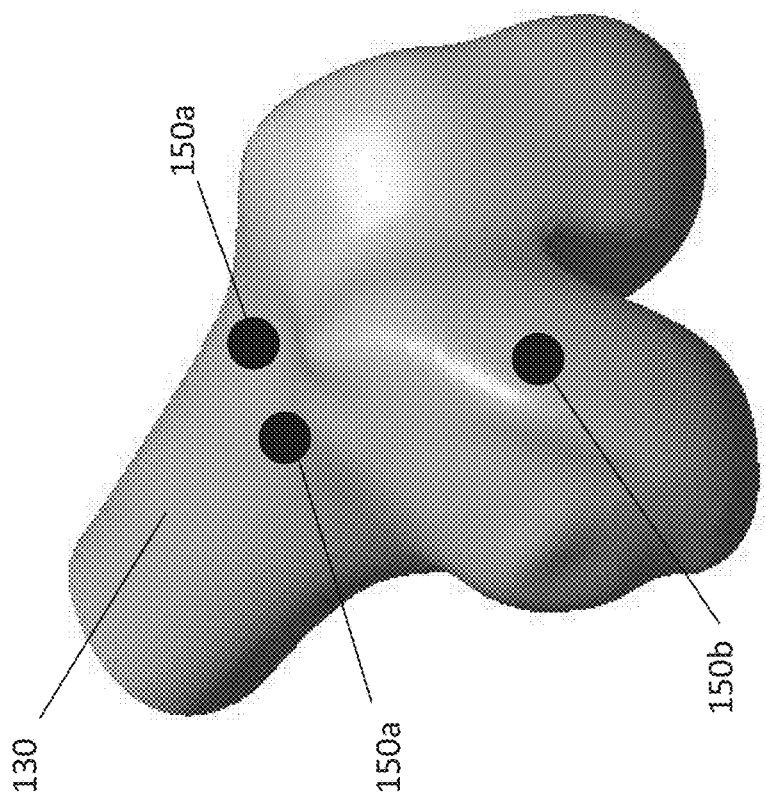
FIG. 4E is a partial perspective view of an alternate configuration of bailout holes created in a femur in the contingency planning phase of FIG. 4A.
Figure 4D:
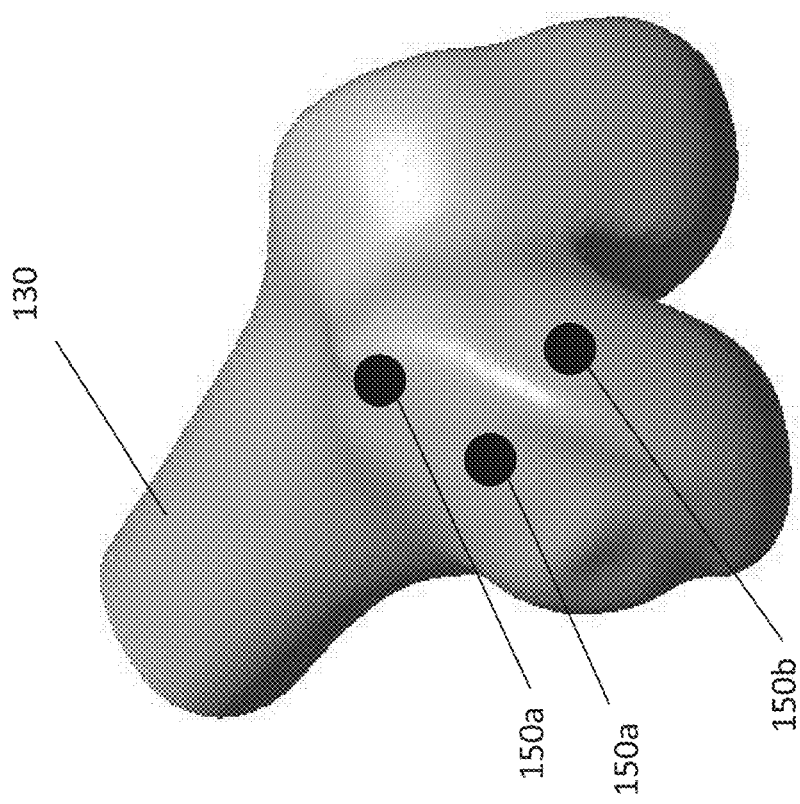
FIG. 4D is a partial perspective view of bailout holes created in a femur in the contingency planning phase of FIG. 4A.

The particular contingency preparation phase 400a illustrated in FIG. 4A takes the form of creating plan points 150, such that a PKR procedure may be completed as a TKA procedure. It should be noted that a different configuration of plan points 150 may be used such that an intended PKR procedure may still be completed as a PKR procedure if the robot 100 fails during the procedure, or if the surgeon otherwise desires to complete the procedure manually. For example, for a PKR to PKR procedure, four plan points may be created in the femur (not illustrated) to interact with a distal resection guide and a 2-in-1 cutting block. For the PKR to TKA procedure, the plan points may take the configurations, for example, as illustrated in FIG. 4D or FIG. 4E. Specifically, the contingency preparation phase 400a begins with step 402, which includes loading a cutting tool 120, such as a router, on the robot 100. In one example, the cutting tool 120 may be a 2.5 mm burr, but other sizes, such as approximately ⅛ inch or approximately 3.175 mm, and other cutting tools may be appropriate. In step 404, the knee is put into flexion, and retractors are positioned in the surgical site. In step 406, registration is performed using femur 130 and tibia 140 trackers 540 to allow the NAV system to guide the robot 100. The surgeon may accept the surgical plan in step 408 if satisfied, touching off key landmarks and verifying placement.

The robot 100 drills three plan points 150 into the femur 130 in step 410. As described above, the particular configuration of plan points 150 may depend on the instruments to be used if the procedure is to be completed manually. As illustrated in FIG. 4D, the three plan points 150 in the femur 130 may include two anterolateral plan points 150a and a distal plan point 150b. All three plan points 150 in the femur 130 are drilled in the particular compartment being replaced. In another embodiment, step 410 may entail drilling two anterior plan points 150a and a distal plan point 150b, as illustrated in FIG. 4E. In step 412, the robot 100 drills two (FIG. 3D) or four (FIG. 2F) plan points 150 into the tibia 140, depending on the preference of the surgeon.

As described with relation to the contingency preparation phases 200a and 300b for the different TKA procedures, the plan points 150 for the PKR procedure may provide references for the surgeon to use if the robot 100 should fail later in the procedure, or if the surgeon otherwise desires to complete the surgical plan manually. For example, the two anterolateral femoral plan points 150a (FIG. 4D) may be sized and positioned to mate with a J-block resection guide 600 or 600', or with a navigated MIS resection guide 500, as shown in FIGS. 4F-K, for example. J-block resection guides 600 are known in the art and described more fully in U.S. Patent Publication No. 2005/0171545, the entire contents of which are hereby incorporated by reference herein. Also as described in relation to other embodiments herein, according to the configuration of plan points 150 illustrated in FIG. 4E, two anterior plan points may be configured to facilitate attachment of a universal resection guide 800 or 800' to the femur 130. In the configuration of plan points 150 illustrated in both FIGS. 4D-E, a distal plan point 150b may be configured to mate with 2-in-1 resection guide (not illustrated). The two anterior tibial plan points 150d may be sized and positioned to mate with a proximal tibial resection guide.

The remaining steps in the PKR procedure are described immediately below according to a successful procedure in which the robot 100 completes the procedure. In the debulking phase 400b, illustrated in FIG. 4B, the first step 414 is to load (or switch to) a cutting tool, such as a barrel burr, onto the robot 100. The cutting tool may be, for example, a 6, 8, or 10 mm barrel burr. However, other sizes and other cutting tools may also be appropriate. In step 416, the distal and posterior chamfer cuts are made on the femur 130. Following these cuts, the proximal tibia 140 and the posterior femur are sequentially debulked. Tissue balancing may be done in step 418 if required. If not required, the surgeon may move to the finishing pass phase 400c. If required, the surgeon may perform tissue balancing as is known in the art. For example, the surgeon may check the tensioning of the knee in flexion and extension, and check the alignment of the mechanical axis using a manual distractor and/or the graphic user interface of the NAV system. If the intraoperative force measurements are acceptable, the surgeon may move to the finishing pass phase 400c. If they are not acceptable, the surgeon may perform soft tissue release. Following the soft tissue release, the surgeon may repeat step 418 for other degrees of freedom of the knee. Alternately, if additional bone surface preparation is required, the surgeon may return to the debulking step 416 after performing the tissue release. Once the surgeon is satisfied with the tissue balancing step 418, he may advance to the finishing pass phase 400c.

In the first step 420 of the finishing pass phase 400c, as illustrated in FIG. 4C, a cutting tool, such as a finishing router, is loaded onto the robot 100. The router may be, for example, a 2.5 mm router, but other sizes and other cutting tools may be appropriate. In step 422, a finishing pass on the femur 130 is completed, for example with the distal/posterior femur and proximal tibia being posed in flexion, between approximately 90 and approximately 110 degrees. In step 424, the proximal tibial preparation is completed, including, for example, preparation of tibial pegs. Finally, the surgeon may complete the procedure by trialing the implant components in step 426 to verify proper size and position, and implanting the components in step 428.

Figure 4F:
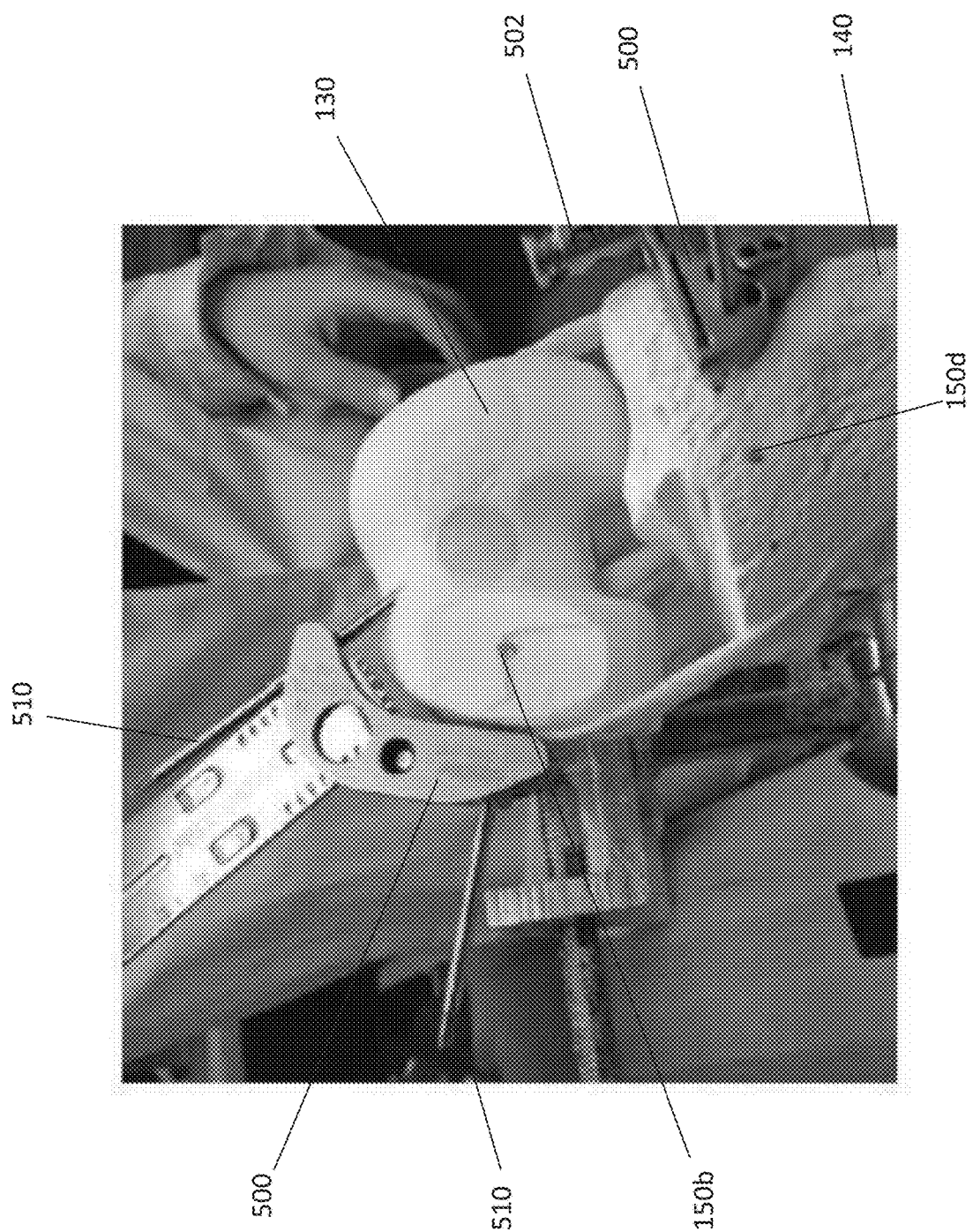
FIG. 4F is a perspective view of a femur and tibia after a robot failed during a robotic PKR procedure.
Figure 4I:
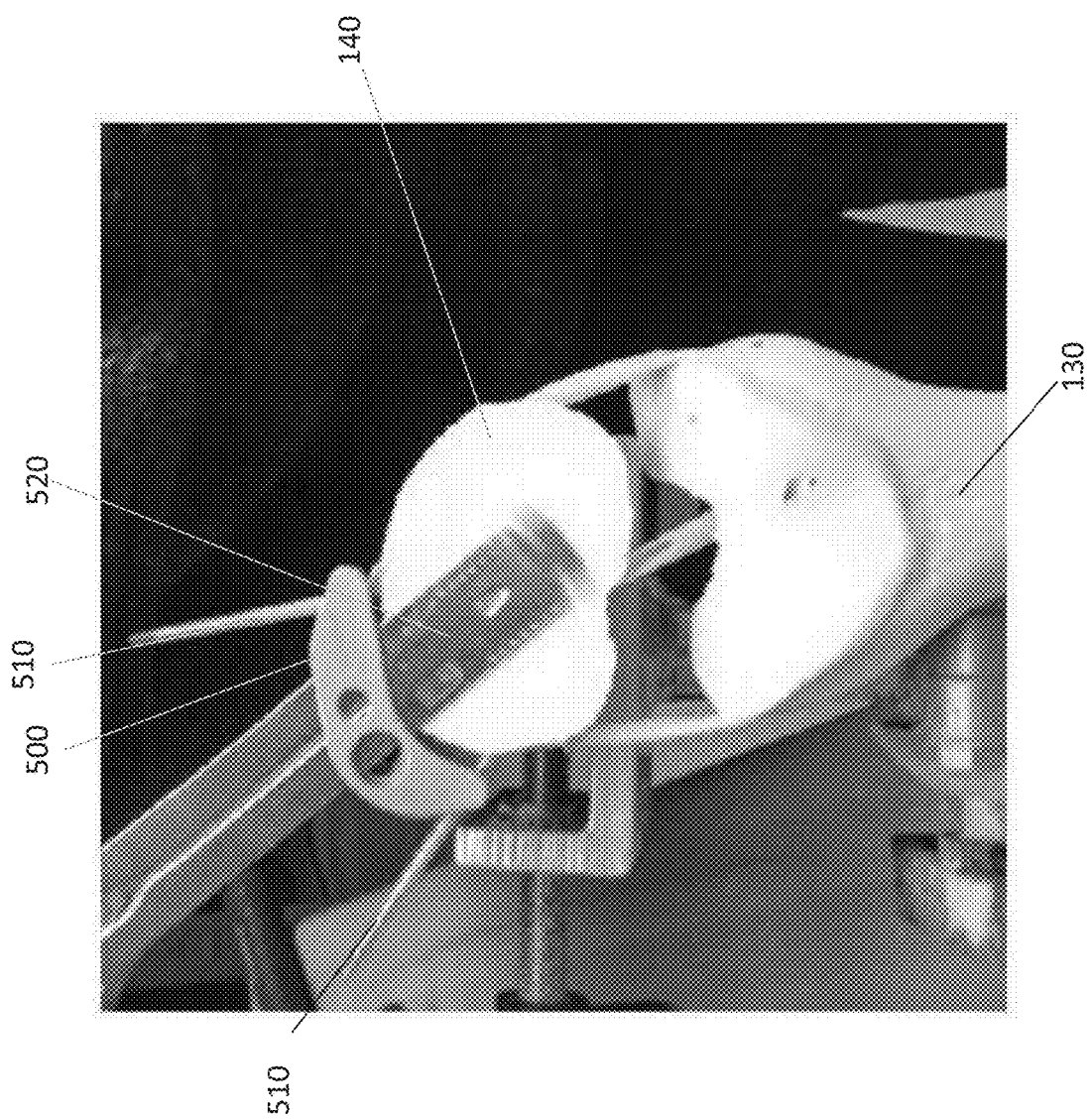
FIG. 4I is a perspective view of a proximal tibial cut being manually performed on the tibia of FIG. 4E using bailout holes.

In the procedure described above for PKR, if the robot 100 and NAV system fail during the procedure after the robot has entered the debulking phase 400b, the surgeon may continue the procedure manually using the plan points 150 as bailout holes, for example as illustrated in FIG. 4D or 4E. Specifically, with reference to FIG. 4F, a femur 130 and tibia 140 are illustrated after plan points 150 are created and at a point which the surgeon decides to complete the procedure manually, in the illustrated case because of a failure of the robot 100. FIG. 4F illustrates the position of the femur 130, with distal femoral plan point 150b visible. Anterolateral plan points configured to mate with a navigated MIS resection guide, similar to the anterolateral plan points 150a of FIG. 4D, are not visible, but fixation pins 510 extend through the navigated MIS resection guide 500 and into the anterolateral plan points 150a. Partially visible in FIG. 4F is another navigated MIS resection guide 500 with tracker adapter 502 (see FIGS. 4J-K) attached to the tibia 140, described in greater detail below. FIG. 4G illustrates a cutting blade 520 being used in conjunction with the navigated MIS resection guide 500 which is held in place by the fixation pins 510 inserted into the anterolateral plan points 150a. The cutting blade 520 is used to manually complete the distal femoral cut, as illustrated in FIG. 4H. FIG. 4I illustrates the tibia 140 with a navigated MIS resection guide 500 attached. Fixation pins 510 are inserted into tibial bailout holes to hold the navigated MIS resection guide 500 in place while a cutting blade 520 is used to resect the proximal tibia 130. As can be seen despite the transition from a robotic to manual procedure mid-surgery, the intended PKR robotic procedure can seamlessly be transitioned into a successful manual TKA procedure by use of the plan points 150 created during the contingency planning phase 400a.

It should be noted that, although particular configurations of plan points are illustrated herein for use with particular types of resection guides, the configuration of the plan points are, at least in part, dictated by the particular jigs, resection guides, or other instruments that need to be attached to the bone using the bailout holes. As such, the methods described herein may be expanded to be used with many other particular resection guides, for example, without departing from the spirit of the invention.

It may also be the case that the robot 100 fails mid-surgery, but the NAV system continues functioning properly. In this scenario, the surgeon may complete the surgery in a similar manner as described directly above, with the aid of the NAV system. For example, FIG. 4J illustrates navigated MIS resection guide 500 with a tracker adapter 502 and tracker 540 attached. The assembly attached to the femur 130 with fixation pins 510 is illustrated in FIG. 4K. Essentially, after the robot 100 fails, the surgery would be completed much as described directly above, but with the additional aid of the NAV system facilitating, for example, the location of the resections. Although surgical procedures using guidance from NAV systems is known in the art, for example in U.S. Pat. Nos. 7,392,076 and 8,382,765, the entire contents of which are hereby incorporated by reference herein, it would be desirable for a surgeon to be able to seamlessly transition from a robotic surgical procedure to a NAV guided manual procedure in the case the robot 100 fails but the NAV system is still operational.

It should be noted that, throughout this disclosure, reference has been made to particular configurations of plan points or bailout holes 150. It should be understood that other configurations are possible, depending on the particular surgical procedure being performed and the particular device to be used with the plan points 150. For example, the plan points 150 may be positioned differently than shown herein to match with the intended location of fixation pins of any appropriate jig to be used in the case of robotic failure. However, as described above, the plan points 150 may also be used in the case in which robotic surgery is not contemplated, but rather wherein a surgeon desires a robot 100 to create plan points 150 that correspond to one or more jigs to be used with the intended manual surgical procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting an implant on a bone comprising:
   providing a robotically controlled bone preparation system;
   performing registration on the bone including fixing a tracker in a fixed configuration with respect to the bone;
   creating at least two bailout holes in the bone;
   wherein the at least two bailout holes are positioned and dimensioned to receive corresponding posts of a manual cutting guide for use in manually resecting the bone when the manual cutting guide is coupled to the bone via the at least two bailout holes, the at least two bailout holes being created only for use if an operator of the robotically controlled bone preparation system desires to transition from an intended procedure that employs the robotically controlled bone preparation system to a contingency procedure that employs the manual cutting guide;
   after creating the at least two bailout holes, cutting the bone using the robotically controlled bone preparation system without the manual cutting guide coupled to the bone and while the tracker is in the fixed configuration with respect to the bone;

after cutting the bone using the robotically controlled bone preparation system, checking the accuracy of the registration and confirming that the tracker has been moved from the fixed configuration with respect to the bone;

after confirming the tracker has been moved from the fixed configuration with respect to the bone, coupling the manual cutting guide to the bone via the at least two bailout holes, and finishing cutting the bone manually with assistance from the manual cutting guide according to the contingency procedure; and after finishing cutting the bone, coupling the implant to the bone.

2. The method of claim 1, wherein after the implant is coupled to the bone, the implant is not received within either of the at least two bailout holes.

3. The method of claim 1, wherein cutting the bone includes removing at least one anatomical landmark of the bone, wherein the at least one anatomical landmark would have been used in determining a position and orientation of the manual cutting guide with respect to the bone.

4. The method of claim 1, wherein the intended procedure and the contingency procedure are both partial knee resections.

5. The method of claim 1, wherein the intended procedure is partial knee resection and the contingency procedure is a total knee arthroplasty.

6. The method of claim 5, wherein the at least two bailout holes includes two anterolateral bailout holes and one distal bailout hole formed in a distal end of a femur.

7. The method of claim 5, wherein the at least two bailout holes includes two anterior bailout holes and one distal bailout hole formed in a distal end of the femur.

8. The method of claim 1, wherein the intended procedure and the contingency procedure are both patellofemoral joint procedures.

9. The method of claim 1, wherein the intended procedure is a patellofemoral joint procedure and the contingency projection is a total knee arthroplasty.

10. The method of claim 1, wherein the intended procedure and the contingency procedure are both total knee arthroplasties.

11. The method of claim 10, wherein the at least two bailout holes includes two anterolateral bailout holes and two distal bailout holes formed in a distal end of a femur.

12. The method of claim 10, wherein the at least two bailout holes includes two anterior bailout holes and two distal bailout holes formed in a distal end of a femur.

13. The method of claim 10, wherein the at least two bailout holes includes two proximal-anterior bailout holes and two proximal bailout holes formed in a proximal end of a tibia.

14. The method of claim 1, wherein finishing cutting the bone manually with assistance from the manual cutting guide according to the contingency procedure includes the use of a navigation system.

15. The method of claim 1, wherein the at least two bailout holes are created using a cutting tool operated by the robotically controlled bone preparation system.

16. The method of claim 1, wherein the at least two bailout holes are created using a cutting tool operated manually.

* * * * *